US007871807B2

(12) United States Patent
Gerdil et al.

(10) Patent No.: US 7,871,807 B2
(45) Date of Patent: Jan. 18, 2011

(54) METHOD FOR PRODUCING THE FLU VIRUS

(75) Inventors: Catherine Gerdil, Tassin la Demi Lune (FR); Catherine Moste, Charbonnieres les Bains (FR); Isabelle Legastelois, Saint Andeol le Chateau (FR); Michel Joseph Marie Bublot, Chaponost (FR); Francois-Xavier Le Gros, Saint Genis Laval (FR)

(73) Assignee: Sanofi Pasteur, S.A., Lyons (FR)

( * ) Notice: Subject to any disclaimer, the term of this patent is extended or adjusted under 35 U.S.C. 154(b) by 270 days.

(21) Appl. No.: 12/238,740

(22) Filed: Sep. 26, 2008

(65) Prior Publication Data
US 2009/0081255 A1 Mar. 26, 2009

Related U.S. Application Data

(60) Provisional application No. 61/063,659, filed on Apr. 2, 2008.

(30) Foreign Application Priority Data

Sep. 26, 2007 (FR) .................................. 07 57884

(51) Int. Cl.
*C12N 7/00* (2006.01)
*C12N 7/02* (2006.01)
*C12N 7/04* (2006.01)
*A61K 39/145* (2006.01)

(52) U.S. Cl. .............. 435/235.1; 424/184.1; 424/209.1; 435/236; 435/239.1

(58) Field of Classification Search ........................ None
See application file for complete search history.

(56) References Cited

U.S. PATENT DOCUMENTS
6,348,197 B1  2/2002  Davelaar

FOREIGN PATENT DOCUMENTS
WO      WO 01/37810    5/2001

OTHER PUBLICATIONS

J.R. Beck et al. Avian Dis. 2003; 47:1196-1199.*
Fontaine et al. Pathobiologie. 1963; 11(9): 611-613.*
Fontaine J. et al.: "Protection of embryonated egg against Influenza infection by a hyperimmune influenza serum," Pathologie-Biologie, vol. 11, No. 9-10, pp. 611-613, May 1963 (translated from French).
M. Coletti et al.: Efficacy and safey of an infectious bursal disease virus intermediate vaccine in ovo, Avian Disease (2001) 45, 1036-1043.
J.E. McCarthy et al.: "Dealy of infectious bursal disease virus infection by in Ovo vaccination of antibody-positive chicken eggs," J. Appl. Poultry. Res. 2005, 14, 136-140.
N. Eterradossi et al.: "Passive protection of specific pathogen free chicks against infectious bursal disease by in-Ovo injection of semi purified egg-yolk antiviral immunoglobulins," J. Vet. Med., 1997, 44, 397-383.
C.A. Ricks et al.: "In Ovo vaccination technology," Advances in Veterinary Medicine, 1999, 41, 495-515.
K.R. Hamal et al.: "Maternal antibody transfer from dams to their egg yolks, egg whites and chicks in meat lines of chickens," Poultry Science 2006, 85, 1364-1372.
H.D. Stone et al.: "Simulation of maternal immunity by inoculation of immune yolk preparations into the yolk sac of 1-day-old chickens," Avian Diseases, 1992, 36, 1048-1051.
Memoranda/Memorandum. Bulletin of the world health Organization 1995, 73(4), 431-435.
D.W. Trampel et al.: "Detection of antibodies in serum and egg yolk following infection of chickens with a H6N2 avian influenza virus," J. Vet. Diagn. Invest., 2006, 18, 437-442.
H.P. Chalumeau: "Vaccine manufacture at the time of a pandemic influenza," European Journal of Epidemiology, 1994, 10, 487-490.
T. Negash et al.: Comparison of in ovo and post-hatch vaccinaton with particular reference to infectious bursal disease (A review). Vetinary quarterly 2004, 26(2), 76-87.
K.Yoshino: "One6day egg culture of animal viruses with special reference to the production of anti-rabies vaccine," Japan J. Med. Sci. Biol. 1967, 20, 111-125.
M.D. Wareing et al.: "Live attenuated vaccines against influenza; an historical review," Vaccine 2001, 19, 3320-3330.
M. Bublot et al.: "Use of a vectored vaccine against infectious bursal disease of chickens in the face of high-titred maternally derived antibody," J. Comp. Path., 2007, 137, S81-S84.
M. Steensels et al.: "Efficacy of an inactivated and a fowlpox-vectored vaccine in Muscovy ducks against an Asian H5N1 highly pathogenic avian Influenza viral challenge," Avian Diseases, 2007, 51, 325-331.
M. Bublot et al.: "Efficay of a flolpox-vectored avian influenza H5 vaccine against Asian H5N1 highly pathogenic avian influenza virus challenge," Avian diseases, 2007, 51, 498-500.

* cited by examiner

*Primary Examiner*—Mary E Mosher
*Assistant Examiner*—Stuart W Snyder
(74) *Attorney, Agent, or Firm*—McDonnell Boehnen Hulbert & Berghoff LLP

(57) ABSTRACT

The invention relates to a method for producing flu virus according to which:
a) immunizing a hen by administering a flu vaccine to the hen,
b) triggering embryogenesis in one or more eggs of the immunized hen,
c) infecting the one or more embryonated eggs by inoculating a flu virus into the allantoic cavity of the eggs,
d) incubating the one or more infected embryonated eggs under temperature and humidity conditions that allow replication of the virus, and
e) harvesting the allantoic fluid of the one or more incubated eggs containing the virus.

19 Claims, 18 Drawing Sheets

FIGURE 1

```
ctaaattgta agcgttaata ttttgttaaa attcgcgtta aattttgtt aaatcagctc    60 atttttaac caataggccg aaatcggcaa aatcccttat aaatcaaaag aatagaccga   120
gatagggttg agtgttgttc cagtttggaa caagagtcca ctattaaaga acgtggactc   180
caacgtcaaa gggcgaaaaa ccgtctatca gggcgatggc ccactacgtg aaccatcacc   240
ctaatcaagt tttttggggt cgaggtgccg taaagcacta aatcggaacc ctaaagggag   300
cccccgattt agagcttgac ggggaaagcc ggcgaacgtg gcgagaaagg aagggaagaa   360
agcgaaagga gcgggcgcta gggcgctggc aagtgtagcg gtcacgctgc gcgtaaccac   420
cacacccgcc gcgcttaatg cgccgctaca gggcgcgtcc cattcgccat tcaggctgcg   480
caactgttgg gaagggcgat cggtgcgggc ctcttcgcta ttacgccagc tggcgaaagg   540
gggatgtgct gcaaggcgat taagttgggt aacgccaggg ttttcccagt cacgacgttg   600
taaaacgacg gccagtgaat tgtaatacga ctcactatag ggcgaattgg gtgacccttt   660
acaagaataa aagaagaaac aactgtgaaa tagtttataa atgtaattcg tatgcagaaa   720
acgataatat attttggtat gagaaatcta aaggagacat agtttgtata gacatgcgct   780
cttccgatga gatattcgat gcttttctaa tgtatcatat agctacaaga tatgcctatc   840
atgatgatga tatatatcta caaatagtgt tatattattc taataatcaa aatgttatat   900
cttatattac gaaaaataaa tacgttaagt atataagaaa taaaactaga gacgatattc   960
ataaagtaaa aatattagct ctagaagact ttacaacgga agaaatatat tgttggatta  1020
gtaatatata acagcgtagc tgcacggttt tgatcatttt ccaacaatat aaaccaatga  1080
aggaggacga ctcatcaaac ataaataaca ttcacggaaa atattcagta tcagatttat  1140
cacaagatga ttatgttatt gaatgtatag acggatcttt tgattcgatc aagtatagag  1200
atataaaggt tataataatg aagaataacg gttacgttaa ttgtagtaaa ttatgtaaaa  1260
tgcggaataa atactttct agatggttgc gtctttctac ttctaaagca ttattagaca  1320
tttacaataa taagtcagta gataatgcta ttgttaaagt ctatggtaaa ggtaagaaac  1380
```

FIGURE 1 (cont'd)

```
ttattataac aggattttat ctcaaacaaa atatgatacg ttatgttatt gagtggatag    1440
gggatgattt tacaaacgat atatacaaaa tgattaattt ctataatgcg ttattcggta    1500
acgatgaatt aaaaatagta tcctgtgaaa acactctatg cccgtttata gaacttggta    1560
gatgctatta tggtaaaaaa tgtaagtata tacacggaga tcaatgtgat atctgtggtc    1620
tatatatact acaccctacc gatattaacc aacgagtttc tcacaagaaa acttgtttag    1680
tagatagaga ttctttgatt gtgtttaaaa gaagtaccag taaaaagtgt ggcatatgca    1740
tagaagaaat aaacaaaaaa catatttccg aacagtattt tggaattctc ccaagttgta    1800
aacatatttt ttgcctatca tgtataagac gttgggcaga tactaccaga aatacagata    1860
ctgaaaatac gtgtcctgaa tgtagaatag ttttccttt cataataccc agtaggtatt     1920
ggatagataa taaatatgat aaaaaaatat tatataatag atataagaaa atgattttta    1980 caaaatacc  tataagaaca ataaaaatat aattacattt acggaaaata gctggtttta    2040
gtttaccaac ttagagtaat tatcatattg aatctatatt gctaattagc taataaaaac    2100
ccgggttaat taattagtca tcaggcaggg cgagaacgag actatctgct cgttaattaa    2160
ttagagcttc tttattctat acttaaaaag tgaaaataaa tacaaaggtt cttgagggtt    2220
gtgttaaatt gaaagcgaga aataatcata aattatttca ttatcgcgat atccgttaag    2280
tttgtatcgt aatggagaaa atcgtgctgc tgctggccat cgtgagcctg gtgaaaagcg    2340
atcagatctg catcggctac cacgccaaca acagcacaga gcaagtggac acaatcatgg    2400
aaaagaacgt gaccgtgaca cacgcccagg acatcctgga aaagacacac aacgggaagc    2460
tgtgcgatct ggatggagtg aagcctctga tcctgagaga ttgcagcgtg gccggatggc    2520
tgctggggaa cccaatgtgc gacgaattca tcaacgtgcc cgaatggagc tacatcgtgg    2580
agaaggccaa cccagccaac gacctgtgct acccagggaa cctgaacgac tacgaagaac    2640
tgaaacacct gctgagcaga atcaaccact tgagaaaat ccagatcatc cccaaaagca    2700
gctggtccga tcacgaagcc agcagcggag tgagcagcgc ctgcccatac cagggaaagt    2760
ccagcttttt tagaaacgtg gtgtggctga tcaaaaagaa cagcgcctac ccaacaatca    2820
```

FIGURE 1 (cont'd)

```
agagaagcta caacaacacc aaccaggaag atctgctggt gctgtggggg atccaccacc   2880
ctaacgatgc cgccgagcag acaaggctgt accagaaccc aaccacctac atctccgtgg   2940
ggacaagcac actgaaccag agactggtgc caaaaatcgc catcagatcc aaagtgaacg   3000
ggcagagcgg aagaatggag ttcttctgga caatcctgaa acccaacgat gccatcaact   3060
tcgagagcaa cggaaacttc atcgccccag aatacgccta caaaatcgtg aagaaggggg   3120
acagcgccat catgaaaagc gaactggaat acggcaactg caacaccaag tgccagaccc   3180 caatggggc catcaacagc agcatgccat tccacaacat ccaccctctg accatcgggg   3240
aatgccccaa atacgtgaaa agcaacagac tggtgctggc caccgggctg agaaacagcc   3300
ctcagagaga gaccagagga ctgtttggag ccatcgccgg ctttatcgag ggaggatggc   3360
agggaatggt ggatggctgg tacggatacc accacagcaa cgagcagggg agcggatacg   3420
ccgccgacaa agaatccacc cagaaggcca tcgacggcgt gaccaacaaa gtgaacagca   3480
tcatcgacaa aatgaacacc cagtttgagg ccgtgggaag ggagtttaac aacctggaaa   3540
ggagaatcga gaacctgaac aagaagatgg aggacggatt cctggatgtg tggacctaca   3600
acgccgaact gctggtgctg atggaaaacg agagaaccct ggactttcac gacagcaacg   3660
tgaagaacct gtacgacaaa gtgaggctgc agctgaggga taacgccaag gagctgggca   3720
acggctgctt cgagttctac cacaaatgcg ataacgaatg catggaaagc atcagaaacg   3780
gaacctacaa ctaccccag tacagcgaag aagccagact gaaaagagaa gaaatctccg   3840
gagtgaaact ggaatccatc ggaacctacc agatcctgag catctacagc acagtggcct   3900
cctccctggc cctggccatc atgatggccg gactgagcct gtggatgtgc tccaacggaa   3960
gcctgcagtg cagaatctgc atctgactcg agttttatt gactagttaa tcataagata   4020
aataatatac agcattgtaa ccatcgtcat ccgttatacg gggaataata ttaccataca   4080
gtattattaa attttcttac gaagaatata gatcggtatt tatcgttagt ttattttaca   4140
tttattaatt aaacatgtct actattacct gttatggaaa tgacaaattt agttatataa   4200
tttatgataa aattaagata ataataatga aatcaaataa ttatgtaaat gctactagat   4260
```

FIGURE 1 (cont'd)

```
tatgtgaatt acgaggaaga aagtttacga actggaaaaa attaagtgaa tctaaaatat    4320
tagtcgataa tgtaaaaaaa ataaatgata aaactaacca gttaaaaacg atatgatta    4380 tatacgttaa ggatattgat cataaaggaa gagatacttg cggttactat gtacaccaag    4440
atctggtatc ttctatatca aattggatat ctccgttatt cgccgttaag gtaaataaaa    4500
ttattaacta ttatatatgt aatgaatatg atatcgact tagcgaaatg gaatctgata    4560
tgacagaagt aatagatgta gttgataaat tagtaggagg atacaatgat gaaatagcag    4620
aaataatata tttgtttaat aaatttatag aaaaatatat tgctaacata tcgttatcaa    4680
ctgaattatc tagtatatta ataattttta taaattttaa taaaaaatac aataacgaca    4740
taaaagatat taaatcttta attcttgatc tgaaaaacac atctataaaa ctagataaaa    4800
agttattcga taaagataat aatgaatcga acgatgaaaa attggaaaca gaagttgata    4860
agctaatttt tttcatctaa atagtattat tttattgaag tacgaagttt tacgttagat    4920
aaataataaa ggtcgatttt tattttgtta aatatcaaat atgtcattat ctgataaaga    4980
tacaaaaaca cacggtgatt atcaaccatc taacgaacag atattacaaa aaatacgtcg    5040
gactatggaa aacgaagctg atagcctcaa tagaagaagc attaaagaaa ttgttgtaga    5100
tgttatgaag aattgggatc atcctctcaa cgaagaaata gataaagttc taaactggaa    5160
aaatgataca ttaaacgatt tagatcatct aaatacagat gataatatta aggaaatcat    5220
acaatgtctg attagagaat ttgcgtttaa aaagatcaat tctattatgt atagttatgc    5280
tatggtaaaa ctcaattcag ataacgaaac attgaaagat aaaattaagg attattttat    5340
agaaactatt cttaaagaca aacgtggtta taaacaaaag ccattaccct agagcggccg    5400
ccaccgcggt ggagctccag cttttgttcc ctttagtgag ggttaatttc gagcttggcg    5460
taatcatggt catagctgtt tcctgtgtga attgttatc cgctcacaat tccacacaac    5520
atacgagccg gaagcataaa gtgtaaagcc tggggtgcct aatgagtgag ctaactcaca    5580
ttaattgcgt tgcgctcact gcccgctttc cagtcgggaa acctgtcgtg ccagctgcat    5640
taatgaatcg gccaacgcgc ggggagaggc ggtttgcgta ttgggcgctc ttccgcttcc    5700
```

FIGURE 1 (cont'd)

```
tcgctcactg actcgctgcg ctcggtcgtt cggctgcggc gagcggtatc agctcactca    5760
aaggcggtaa tacggttatc cacagaatca ggggataacg caggaaagaa catgtgagca    5820
aaaggccagc aaaaggccag gaaccgtaaa aaggccgcgt tgctggcgtt tttccatagg    5880
ctccgccccc ctgacgagca tcacaaaaat cgacgctcaa gtcagaggtg gcgaaacccg    5940
acaggactat aaagatacca ggcgtttccc cctggaagct ccctcgtgcg ctctcctgtt    6000
ccgaccctgc cgcttaccgg atacctgtcc gcctttctcc cttcgggaag cgtggcgctt    6060
tctcatagct cacgctgtag gtatctcagt tcggtgtagg tcgttcgctc caagctgggc    6120
tgtgtgcacg aaccccccgt tcagcccgac cgctgcgcct tatccggtaa ctatcgtctt    6180
gagtccaacc cggtaagaca cgacttatcg ccactggcag cagccactgg taacaggatt    6240
agcagagcga ggtatgtagg cggtgctaca gagttcttga agtggtggcc taactacggc    6300
tacactagaa ggacagtatt tggtatctgc gctctgctga gccagttac cttcggaaaa     6360 agagttggta gctcttgatc cggcaaacaa accaccgctg gtagcggtgg ttttttttgtt    6420 tgcaagcagc agattacgcg cagaaaaaaa ggatctcaag aagatccttt gatcttttct    6480
acggggtctg acgctcagtg gaacgaaaac tcacgttaag ggattttggt catgagatta    6540
tcaaaaagga tcttcaccta gatcctttta aattaaaaat gaagttttaa atcaatctaa    6600
agtatatatg agtaaacttg gtctgacagt taccaatgct taatcagtga ggcacctatc    6660
tcagcgatct gtctatttcg ttcatccata gttgcctgac tccccgtcgt gtagataact    6720
acgatacggg agggcttacc atctggcccc agtgctgcaa tgataccgcg agacccacgc    6780
tcaccggctc cagatttatc agcaataaac cagccagccg aagggccga gcgcagaagt      6840 ggtcctgcaa ctttatccgc ctccatccag tctattaatt gttgccggga agctagagta    6900
agtagttcgc cagttaatag tttgcgcaac gttgttgcca ttgctacagg catcgtggtg    6960
tcacgctcgt cgtttggtat ggcttcattc agctccggtt cccaacgatc aaggcgagtt    7020
acatgatccc ccatgttgtg caaaaaagcg gttagctcct tcggtcctcc gatcgttgtc    7080
agaagtaagt tggccgcagt gttatcactc atggttatgg cagcactgca taattctctt    7140
```

FIGURE 1 (cont'd)

```
actgtcatgc catccgtaag atgcttttct gtgactggtg agtactcaac caagtcattc    7200
tgagaatagt gtatgcggcg accgagttgc tcttgcccgg cgtcaatacg ggataatacc    7260
gcgccacata gcagaacttt aaaagtgctc atcattggaa aacgttcttc ggggcgaaaa    7320
ctctcaagga tcttaccgct gttgagatcc agttcgatgt aacccactcg tgcacccaac    7380
tgatcttcag catcttttac tttcaccagc gtttctgggt gagcaaaaac aggaaggcaa    7440
aatgccgcaa aaagggaat aagggcgaca cggaaatgtt gaatactcat actcttcctt    7500
tttcaatatt attgaagcat ttatcagggt tattgtctca tgagcggata catatttgaa    7560
tgtatttaga aaataaaca aatagggggtt ccgcgcacat ttccccgaaa agtgccac     7618
```

1 GTAAAACGAC GGCCAGTGAA TTGTAATACG ACTCACTATA GGGCGAATTG
   CATTTTGCTG CCGGTCACTT AACATTATGC TGAGTGATAT CCCGCTTAAC

51 GGTGACCCTT TACAAGAATA AAGAAGAAA CAACTGTGAA ATAGTTTATA
   CCACTGGGAA ATGTTCTTAT TTCTTCTTT GTTGACACTT TATCAAATAT

101 AATGTAATTC GTATGCAGAA AACGATAATA TATTTTGGTA TGAGAAATCT
    TTACATTAAG CATACGTCTT TTGCTATTAT ATAAAACCAT ACTCTTTAGA

151 AAAGGAGACA TAGTTTGTAT AGACATGCGC TCTTCCGATG AGATATTCGA
    TTTCCTCTGT ATCAAACATA TCTGTACGCG AGAAGGCTAC TCTATAAGCT

201 TGCTTTTCTA ATGTATCATA TAGCTACAAG ATATGCCTAT CATGATGATG
    ACGAAAAGAT TACATAGTAT ATCGATGTTC TATACGGATA GTACTACTAC

251 ATATATATCT ACAAATAGTG TTATATTATT CTAATAATCA AAATGTTATA
    TATATATAGA TGTTTATCAC AATATAATAA GATTATTAGT TTTACAATAT

301 TCTTATATTA CGAAAAATAA ATACGTTAAG TATATAAGAA ATAAAACTAG
    AGAATATAAT GCTTTTTATT TATGCAATTC ATATATTCTT TATTTTGATC

351 AGACGATATT CATAAAGTAA AAATATTAGC TCTAGAAGAC TTTACAACGG
    TCTGCTATAA GTATTTCATT TTTATAATCG AGATCTTCTG AAATGTTGCC

401 AAGAAATATA TTGTTGGATT AGTAATATAT AACAGCGTAG CTGCACGGTT
    TTCTTTATAT AACAACCTAA TCATTATATA TTGTCGCATC GACGTGCCAA

451 TTGATCATTT TCCAACAATA TAAACCAATG AAGGAGGACG ACTCATCAAA
    AACTAGTAAA AGGTTGTTAT ATTTGGTTAC TTCCTCCTGC TGAGTAGTTT

FIGURE 2 (cont'd)

```
 501 CATAAATAAC ATTCACGGAA AATATTCAGT ATCAGATTTA TCACAAGATG
     GTATTTATTG TAAGTGCCTT TTATAAGTCA TAGTCTAAAT AGTGTTCTAC
 551 ATTATGTTAT TGAATGTATA GACGGATCTT TTGATTCGAT CAAGTATAGA
     TAATACAATA ACTTACATAT CTGCCTAGAA AACTAAGCTA GTTCATATCT
 601 GATATAAAGG TTATAATAAT GAAGAATAAC GGTTACGTTA ATTGTAGTAA
     CTATATTTCC AATATTATTA CTTCTTATTG CCAATGCAAT TAACATCATT
 651 ATTATGTAAA ATGCGGAATA AATACTTTTC TAGATGGTTG CGTCTTTCTA
     TAATACATTT TACGCCTTAT TTATGAAAAG ATCTACCAAC GCAGAAAGAT
 701 CTTCTAAAGC ATTATTAGAC ATTTACAATA ATAAGTCAGT AGATAATGCT
     GAAGATTTCG TAATAATCTG TAAATGTTAT TATTCAGTCA TCTATTACGA
 751 ATTGTTAAAG TCTATGGTAA AGGTAAGAAA CTTATTATAA CAGGATTTTA
     TAACAATTTC AGATACCATT TCCATTCTTT GAATAATATT GTCCTAAAAT
 801 TCTCAAACAA AATATGATAC GTTATGTTAT TGAGTGGATA GGGGATGATT
     AGAGTTTGTT TTATACTATG CAATACAATA ACTCACCTAT CCCCTACTAA
 851 TTACAAACGA TATATACAAA ATGATTAATT TCTATAATGC GTTATTCGGT
     AATGTTTGCT ATATATGTTT TACTAATTAA AGATATTACG CAATAAGCCA
 901 AACGATGAAT TAAAAATAGT ATCCTGTGAA AACACTCTAT GCCCGTTTAT
     TTGCTACTTA ATTTTATCA TAGGACACTT TTGTGAGATA CGGGCAAATA
 951 AGAACTTGGT AGATGCTATT ATGGTAAAAA ATGTAAGTAT ATACACGGAG
     TCTTGAACCA TCTACGATAA TACCATTTTT TACATTCATA TATGTGCCTC
1001 ATCAATGTGA TATCTGTGGT CTATATATAC TACACCCTAC CGATATTAAC
     TAGTTACACT ATAGACACCA GATATATATG ATGTGGGATG GCTATAATTG
```

FIGURE 2 (cont'd)

```
1051 CAACGAGTTT CTCACAAGAA AACTTGTTTA GTAGATAGAG ATTCTTTGAT
     GTTGCTCAAA GAGTGTTCTT TTGAACAAAT CATCTATCTC TAAGAAACTA
1101 TGTGTTTAAA AGAAGTACCA GTAAAAGTG TGGCATATGC ATAGAAGAAA
     ACACAAATTT TCTTCATGGT CATTTTTCAC ACCGTATACG TATCTTCTTT
1151 TAAACAAAAA ACATATTTCC GAACAGTATT TTGGAATTCT CCCAAGTTGT
     ATTTGTTTTT TGTATAAAGG CTTGTCATAA AACCTTAAGA GGGTTCAACA
1201 AAACATATTT TTTGCCTATC ATGTATAAGA CGTTGGGCAG ATACTACCAG
     TTTGTATAAA AAACGGATAG TACATATTCT GCAACCCGTC TATGATGGTC
1251 AAATACAGAT ACTGAAAATA CGTGTCCTGA ATGTAGAATA GTTTTTCCTT
     TTTATGTCTA TGACTTTTAT GCACAGGACT TACATCTTAT CAAAAAGGAA
1301 TCATAATACC CAGTAGGTAT TGGATAGATA ATAAATATGA TAAAAAAATA
     AGTATTATGG GTCATCCATA ACCTATCTAT TATTTATACT ATTTTTTTAT
1351 TTATATAATA GATATAAGAA AATGATTTTT ACAAAAATAC CTATAAGAAC
     AATATATTAT CTATATTCTT TTACTAAAAA TGTTTTTATG GATATTCTTG
1401 AATAAAAATA TAATTACATT TACGGAAAAT AGCTGGTTTT AGTTTACCAA
     TTATTTTTAT ATTAATGTAA ATGCCTTTTA TCGACCAAAA TCAAATGGTT
1451 CTTAGAGTAA TTATCATATT GAATCTATAT TGCTAATTAG CTAATAAAAA
     GAATCTCATT AATAGTATAA CTTAGATATA CGATTAATC GATTATTTTT
1501 CCCGGGTTAA TTAATTAGTC ATCAGGCAGG GCGAGAACGA GACTATCTGC
     GGGCCCAATT AATTAATCAG TAGTCCGTCC CGCTCTTGCT CTGATAGACG
1551 TCGTTAATTA ATTAGAGCTT CTTTATTCTA TACTTAAAAA GTGAAAATAA
     AGCAATTAAT TAATCTCGAA GAAATAAGAT ATGAATTTTT CACTTTTATT
```

FIGURE 2 (cont'd)

```
1601 ATACAAAGGT TCTTGAGGGT TGTGTTAAAT TGAAAGCGAG AAATAATCAT
     TATGTTTCCA AGAACTCCCA ACACAATTTA ACTTTCGCTC TTTATTAGTA

M   E   K ·
1651 AAATTATTTC ATTATCGCGA TATCCGTTAA GTTTGTATCG TAATGGAGAA
     TTTAATAAAG TAATAGCGCT ATAGGCAATT CAAACATAGC ATTACCTCTT

· I   V   L   L   A   I   V   S   L   V   K   S   D   Q   I   C ·
1701 AATCGTGCTG CTGCTGGCCA TCGTGAGCCT GGTGAAAAGC GATCAGATCT
     TTAGCACGAC GACGACCGGT AGCACTCGGA CCACTTTTCG CTAGTCTAGA

· · I   G   Y   H   A   N   N   S   T   E   Q   V   D   T   I   M
1751 GCATCGGCTA CCACGCCAAC AACAGCACAG AGCAAGTGGA CACAATCATG
     CGTAGCCGAT GGTGCGGTTG TTGTCGTGTC TCGTTCACCT GTGTTAGTAC

E   K   N   V   T   V   T   H   A   Q   D   I   L   E   K   T   H ·
1801 GAAAAGAACG TGACCGTGAC ACACGCCCAG GACATCCTGG AAAAGACACA
     CTTTTCTTGC ACTGGCACTG TGTGCGGGTC CTGTAGGACC TTTTCTGTGT

· N   G   K   L   C   D   L   D   G   V   K   P   L   I   L   R   D ·
1851 CAACGGGAAG CTGTGCGATC TGGATGGAGT GAAGCCTCTG ATCCTGAGAG
     GTTGCCCTTC GACACGCTAG ACCTACCTCA CTTCGGAGAC TAGGACTCTC
```

FIGURE 2 (cont'd)

```
     ..  C    S    V    A    G    W    L    L    G    N    P    M    C    D    E    F
1901 ATTGCAGCGT GGCCGGATGG CTGCTGGGGA ACCCAATGTG CGACGAATTC
     TAACGTCGCA CCGGCCTACC GACGACCCCT TGGGTTACAC GCTGCTTAAG

I    N    V    P    E    W    S    Y    I    V    E    K    A    N    P    A    N ·
1951 ATCAACGTGC CCGAATGGAG CTACATCGTG GAGAAGGCCA ACCCAGCCAA
     TAGTTGCACG GGCTTACCTC GATGTAGCAC CTCTTCCGGT TGGGTCGGTT

· D    L    C    Y    P    G    N    L    N    D    Y    E    E    L    K    H    L ·
2001 CGACCTGTGC TACCCAGGGA ACCTGAACGA CTACGAAGAA CTGAAACACC
     GCTGGACACG ATGGGTCCCT TGGACTTGCT GATGCTTCTT GACTTTGTGG

..  L    S    R    I    N    H    F    E    K    I    Q    I    I    P    K    S
2051 TGCTGAGCAG AATCAACCAC TTTGAGAAAA TCCAGATCAT CCCCAAAAGC
     ACGACTCGTC TTAGTTGGTG AAACTCTTTT AGGTCTAGTA GGGGTTTTCG

S    W    S    D    H    E    A    S    S    G    V    S    S    A    C    P    Y ·
2101 AGCTGGTCCG ATCACGAAGC CAGCAGCGGA GTGAGCAGCG CCTGCCCATA
     TCGACCAGGC TAGTGCTTCG GTCGTCGCCT CACTCGTCGC GGACGGGTAT
```

FIGURE 2 (cont'd)

```
           .  Q    G    K    S    S    F    F    R    N    V    V    W    L    I    K    K    N  ·
      2151 CCAGGGAAAG TCCAGCTTTT TTAGAAACGT GGTGTGGCTG ATCAAAAAGA
           GGTCCCTTTC AGGTCGAAAA AATCTTTGCA CCACACCGAC TAGTTTTTCT

..  S    A    Y    P    T    I    K    R    S    Y    N    N    T    N    Q    E
      2201 ACAGCGCCTA CCCAACAATC AAGAGAAGCT ACAACAACAC CAACCAGGAA
           TGTCGCGGAT GGGTTGTTAG TTCTCTTCGA TGTTGTTGTG GTTGGTCCTT

D    L    L    V    L    W    G    I    H    H    P    N    D    A    A    E    Q  ·
      2251 GATCTGCTGG TGCTGTGGGG GATCCACCAC CCTAACGATG CCGCCGAGCA
           CTAGACGACC ACGACACCCC CTAGGTGGTG GGATTGCTAC GGCGGCTCGT

.  T    R    L    Y    Q    N    P    T    T    Y    I    S    V    G    T    S    T  ·
      2301 GACAAGGCTG TACCAGAACC CAACCACCTA CATCTCCGTG GGGACAAGCA
           CTGTTCCGAC ATGGTCTTGG GTTGGTGGAT GTAGAGGCAC CCCTGTTCGT

..  L    N    Q    R    L    V    P    K    I    A    I    R    S    K    V    N
      2351 CACTGAACCA GAGACTGGTG CCAAAAATCG CCATCAGATC CAAAGTGAAC
           GTGACTTGGT CTCTGACCAC GGTTTTTAGC GGTAGTCTAG GTTTCACTTG

G    Q    S    G    R    M    E    F    F    W    T    I    L    K    P    N    D  ·
      2401 GGGCAGAGCG GAAGAATGGA GTTCTTCTGG ACAATCCTGA AACCCAACGA
           CCCGTCTCGC CTTCTTACCT CAAGAAGACC TGTTAGGACT TTGGGTTGCT

.  A    I    N    F    E    S    N    G    N    F    I    A    P    E    Y    A    Y  ·
      2451 TGCCATCAAC TTCGAGAGCA ACGGAAACTT CATCGCCCCA GAATACGCCT
           ACGGTAGTTG AAGCTCTCGT TGCCTTTGAA GTAGCGGGGT CTTATGCGGA
```

FIGURE 2 (cont'd)

```
        ..K   I   V   K   K   G   D   S   A   I   M   K   S   E   L   E
2501 ACAAAATCGT GAAGAAAGGG GACAGCGCCA TCATGAAAAG CGAACTGGAA
     TGTTTTAGCA CTTCTTTCCC CTGTCGCGGT AGTACTTTTC GCTTGACCTT
          Y   G   N   C   N   T   K   C   Q   T   P   M   G   A   I   N   S·
2551 TACGGCAACT GCAACACCAA GTGCCAGACC CCAATGGGGG CCATCAACAG
     ATGCCGTTGA CGTTGTGGTT CACGGTCTGG GGTTACCCCC GGTAGTTGTC
         ·S   M   P   F   H   N   I   H   P   L   T   I   G   E   C   P   K·
2601 CAGCATGCCA TTCCACAACA TCCACCCTCT GACCATCGGG GAATGCCCCA
     GTCGTACGGT AAGGTGTTGT AGGTGGGAGA CTGGTAGCCC CTTACGGGGT
        ..Y   V   K   S   N   R   L   V   L   A   T   G   L   R   N   S
2651 AATACGTGAA AAGCAACAGA CTGGTGCTGG CCACCGGGCT GAGAAACAGC
     TTATGCACTT TTCGTTGTCT GACCACGACC GGTGGCCCGA CTCTTTGTCG
          P   Q   R   E   T   R   G   L   F   G   A   I   A   G   F   I   E·
2701 CCTCAGAGAG AGACCAGAGG ACTGTTTGGA GCCATCGCCG GCTTTATCGA
     GGAGTCTCTC TCTGGTCTCC TGACAAACCT CGGTAGCGGC CGAAATAGCT
         ·G   G   W   Q   G   M   V   D   G   W   Y   G   Y   H   H   S   N·
2751 GGGAGGATGG CAGGGAATGG TGGATGGCTG GTACGGATAC CACCACAGCA
     CCCTCCTACC GTCCCTTACC ACCTACCGAC CATGCCTATG GTGGTGTCGT
        ..E   Q   G   S   G   Y   A   A   D   K   E   S   T   Q   K   A
2801 ACGAGCAGGG GAGCGGATAC GCCGCCGACA AGAATCCAC CCAGAAGGCC
     TGCTCGTCCC CTCGCCTATG CGGCGGCTGT TCTTAGGTG GGTCTTCCGG
```

FIGURE 2 (cont'd)

```
              I   D   G   V   T   N   K   V   N   S   I   I   D   K   M   N   T  ·
2851 ATCGACGGCG TGACCAACAA AGTGAACAGC ATCATCGACA AAATGAACAC
     TAGCTGCCGC ACTGGTTGTT TCACTTGTCG TAGTAGCTGT TTTACTTGTG

· Q   F   E   A   V   G   R   E   F   N   N   L   E   R   R   I   E  ·
2901 CCAGTTTGAG GCCGTGGGAA GGGAGTTTAA CAACCTGGAA AGGAGAATCG
     GGTCAAACTC CGGCACCCTT CCCTCAAATT GTTGGACCTT TCCTCTTAGC

·· N   L   N   K   K   M   E   D   G   F   L   D   V   W   T   Y
2951 AGAACCTGAA CAAGAAGATG GAGGACGGAT TCCTGGATGT GTGGACCTAC
     TCTTGGACTT GTTCTTCTAC CTCCTGCCTA AGGACCTACA CACCTGGATG

N   A   E   L   L   V   L   M   E   N   E   R   T   L   D   F   H  ·
3001 AACGCCGAAC TGCTGGTGCT GATGGAAAAC GAGAGAACCC TGGACTTTCA
     TTGCGGCTTG ACGACCACGA CTACCTTTTG CTCTCTTGGG ACCTGAAAGT

· D   S   N   V   K   N   L   Y   D   K   V   R   L   Q   L   R   D  ·
3051 CGACAGCAAC GTGAAGAACC TGTACGACAA AGTGAGGCTG CAGCTGAGGG
     GCTGTCGTTG CACTTCTTGG ACATGCTGTT TCACTCCGAC GTCGACTCCC

·· N   A   K   E   L   G   N   G   C   F   E   F   Y   H   K   C
3101 ATAACGCCAA GGAGCTGGGC AACGGCTGCT TCGAGTTCTA CCACAAATGC
     TATTGCGGTT CCTCGACCCG TTGCCGACGA AGCTCAAGAT GGTGTTTACG

D   N   E   C   M   E   S   I   R   N   G   T   Y   N   Y   P   Q  ·
3151 GATAACGAAT GCATGGAAAG CATCAGAAAC GGAACCTACA ACTACCCCCA
     CTATTGCTTA CGTACCTTTC GTAGTCTTTG CCTTGGATGT TGATGGGGGT
```

FIGURE 2 (cont'd)

```
         . Y    S    E     E    A    R    L     K    R    E      E    I    S      G    V    K    L ·
3201 GTACAGCGAA GAAGCCAGAC TGAAAAGAGA AGAAATCTCC GGAGTGAAAC
     CATGTCGCTT CTTCGGTCTG ACTTTTCTCT TCTTTAGAGG CCTCACTTTG

.. E    S    I      G    T    Y      Q    I    L    S      I    Y    S       T    V    A
3251 TGGAATCCAT CGGAACCTAC CAGATCCTGA GCATCTACAG CACAGTGGCC
     ACCTTAGGTA GCCTTGGATG GTCTAGGACT CGTAGATGTC GTGTCACCGG

S    S    L    A     L    A    I      M    M    A      G    L    S       W    M    C ·
3301 TCCTCCCTGG CCCTGGCCAT CATGATGGCC GGACTGAGCC TGTGGATGTG
     AGGAGGGACC GGGACCGGTA GTACTACCGG CCTGACTCGG ACACCTACAC

. S    N    G     S    L    Q    C     R    I    C      I  *
3351 CTCCAACGGA AGCCTGCAGT GCAGAATCTG CATCTGACTC GAGTTTTTAT
     GAGGTTGCCT TCGGACGTCA CGTCTTAGAC GTAGACTGAG CTCAAAAATA

3401 TGACTAGTTA ATCATAAGAT AAATAATATA CAGCATTGTA ACCATCGTCA
     ACTGATCAAT TAGTATTCTA TTTATTATAT GTCGTAACAT TGGTAGCAGT

3451 TCCGTTATAC GGGGAATAAT ATTACCATAC AGTATTATTA AATTTTCTTA
     AGGCAATATG CCCCTTATTA TAATGGTATG TCATAATAAT TTAAAGAAT
```

FIGURE 2 (cont'd)

```
3501 CGAAGAATAT AGATCGGTAT TTATCGTTAG TTTATTTTAC ATTTATTAAT
     GCTTCTTATA TCTAGCCATA AATAGCAATC AAATAAAATG TAAATAATTA
3551 TAAACATGTC TACTATTACC TGTTATGGAA ATGACAAATT TAGTTATATA
     ATTTGTACAG ATGATAATGG ACAATACCTT TACTGTTTAA ATCAATATAT
3601 ATTTATGATA AAATTAAGAT AATAATAATG AAATCAAATA ATTATGTAAA
     TAAATACTAT TTTAATTCTA TTATTATTAC TTTAGTTTAT TAATACATTT
3651 TGCTACTAGA TTATGTGAAT TACGAGGAAG AAAGTTTACG AACTGGAAAA
     ACGATGATCT AATACACTTA ATGCTCCTTC TTTCAAATGC TTGACCTTTT
3701 AATTAAGTGA ATCTAAAATA TTAGTCGATA ATGTAAAAAA AATAAATGAT
     TTAATTCACT TAGATTTTAT AATCAGCTAT TACATTTTTT TTATTTACTA
3751 AAAACTAACC AGTTAAAAAC GGATATGATT ATATACGTTA AGGATATTGA
     TTTTGATTGG TCAATTTTTG CCTATACTAA TATATGCAAT TCCTATAACT
3801 TCATAAAGGA AGAGATACTT GCGGTTACTA TGTACACCAA GATCTGGTAT
     AGTATTTCCT TCTCTATGAA CGCCAATGAT ACATGTGGTT CTAGACCATA
3851 CTTCTATATC AAATTGGATA TCTCCGTTAT TCGCCGTTAA GGTAAATAAA
     GAAGATATAG TTTAACCTAT AGAGGCAATA AGCGGCAATT CCATTTATTT
3901 ATTATTAACT ATTATATATG TAATGAATAT GATATACGAC TTAGCGAAAT
     TAATAATTGA TAATATATAC ATTACTTATA CTATATGCTG AATCGCTTTA
3951 GGAATCTGAT ATGACAGAAG TAATAGATGT AGTTGATAAA TTAGTAGGAG
     CCTTAGACTA TACTGTCTTC ATTATCTACA TCAACTATTT AATCATCCTC
4001 GATACAATGA TGAAATAGCA GAAATAATAT ATTTGTTTAA TAAATTTATA
     CTATGTTACT ACTTTATCGT CTTTATTATA TAAACAAATT ATTTAAATAT
```

FIGURE 2 (cont'd)

```
4051 GAAAAATATA TTGCTAACAT ATCGTTATCA ACTGAATTAT CTAGTATATT
     CTTTTTATAT AACGATTGTA TAGCAATAGT TGACTTAATA GATCATATAA
4101 AAATAATTTT ATAAATTTTA ATAAAAAATA CAATAACGAC ATAAAAGATA
     TTTATTAAAA TATTTAAAAT TATTTTTTAT GTTATTGCTG TATTTTCTAT
4151 TTAAATCTTT AATTCTTGAT CTGAAAAACA CATCTATAAA ACTAGATAAA
     AATTTAGAAA TTAAGAACTA GACTTTTGT GTAGATATTT TGATCTATTT
4201 AAGTTATTCG ATAAAGATAA TAATGAATCG AACGATGAAA AATTGGAAAC
     TTCAATAAGC TATTTCTATT ATTACTTAGC TTGCTACTTT TAACCTTTG
4251 AGAAGTTGAT AAGCTAATTT TTTTCATCTA AATAGTATTA TTTTATTGAA
     TCTTCAACTA TTCGATTAAA AAAGTAGAT TTATCATAAT AAAATAACTT
4301 GTACGAAGTT TTACGTTAGA TAAATAATAA AGGTCGATTT TTATTTTGTT
     CATGCTTCAA AATGCAATCT ATTTATTATT TCCAGCTAAA AATAAAACAA
4351 AAATATCAAA TATGTCATTA TCTGATAAAG ATACAAAAAC ACACGGTGAT
     TTTATAGTTT ATACAGTAAT AGACTATTTC TATGTTTTTG TGTGCCACTA
4401 TATCAACCAT CTAACGAACA GATATTACAA AAAATACGTC GGACTATGGA
     ATAGTTGGTA GATTGCTTGT CTATAATGTT TTTTATGCAG CCTGATACCT
4451 AAACGAAGCT GATAGCCTCA ATAGAAGAAG CATTAAAGAA ATTGTTGTAG
     TTTGCTTCGA CTATCGGAGT TATCTTCTTC GTAATTTCTT TAACAACATC
4501 ATGTTATGAA GAATTGGGAT CATCCTCTCA ACGAAGAAAT AGATAAAGTT
     TACAATACTT CTTAACCCTA GTAGGAGAGT TGCTTCTTTA TCTATTTCAA
4551 CTAAACTGGA AAAATGATAC ATTAAACGAT TTAGATCATC TAAATACAGA
     GATTTGACCT TTTTACTATG TAATTTGCTA AATCTAGTAG ATTTATGTCT
```

FIGURE 2 (cont'd)

```
4601 TGATAATATT AAGGAAATCA TACAATGTCT GATTAGAGAA TTTGCGTTTA
     ACTATTATAA TTCCTTTAGT ATGTTACAGA CTAATCTCTT AAACGCAAAT
4651 AAAAGATCAA TTCTATTATG TATAGTTATG CTATGGTAAA ACTCAATTCA
     TTTTCTAGTT AAGATAATAC ATATCAATAC GATACCATTT TGAGTTAAGT
4701 GATAACGAAA CATTGAAAGA TAAAATTAAG GATTATTTTA TAGAAACTAT
     CTATTGCTTT GTAACTTTCT ATTTTAATTC CTAATAAAAT ATCTTTGATA
4751 TCTTAAAGAC AAACGTGGTT ATAAACAAAA GCCATTACCC TAGAGCGGCC
     AGAATTTCTG TTTGCACCAA TATTTGTTTT CGGTAATGGG ATCTCGCCGG
4801 GCCACCGCGG TGGAGCTCCA GCTTTTGTTC CCTTTAGTGA GGGTTAATTT
     CGGTGGCGCC ACCTCGAGGT CGAAACAAG GGAAATCACT CCCAATTAAA
4851 CGAGCTTGGC GTAATCATGG TCATAGCTGT TTCCT
     GCTCGAACCG CATTAGTACC AGTATCGACA AAGGA
                        M13R
```

METHOD FOR PRODUCING THE FLU VIRUS

CROSS-REFERENCE TO RELATED APPLICATIONS

This application claims the benefit of priority of U.S. provisional application 61/063,659, filed Feb. 4, 2008.

BACKGROUND OF THE INVENTION

1. Field of the Invention

The invention relates to a method for producing the flu virus using eggs originating from hens immunized against the flu and also to the use of such a method for the manufacture of a flu vaccine.

2. Summary of the Related Art

Three types of flu virus (A, B and C) are currently known, the type A viruses being responsible for animal and human conditions while the type B and type C viruses are especially pathogenic for humans. The type A viruses are subdivided into subtypes according to the antigenic structure of hemagglutinin (HA) and of neuraminidase (NA) which are the principal glycoproteins of the viral envelope. Sixteen subtypes of HA (H1 to H16) and 9 subtypes of NA (N1 to N9) stand out. The subtype of a type A virus is therefore defined by the HA subtype and the NA subtype which are present in the viral envelope. Wild birds constitute the reservoir of all influenza A subtypes. Certain subtypes of influenza virus type A endemically or epidemically (annual epidemics) infect domestic birds (various subtypes including H5N1 and H9N2), horses (principally H3N8), pigs (principally H1N1, H3N2 and H1N2) and also humans (principally H1N1 and H3N2). Dogs, cats and other wild species can also occasionally be infected with certain subtypes (H3N8 and H5N1 in dogs; H5N1 in cats).

In the veterinary field, poultry farms, and more particularly chicks, chickens, hens and roosters, represent in terms of number the largest population liable to be affected by the flu virus. The avian flu strains of subtypes H5 and H7 may be of two pathotypes: a low path (or LP) pathotype and a high path (or HP) pathotype. The HP strains are responsible for avian flu and derive from the LP strains H5 and H7 after mutations/insertions in particular at the hemagglutinin cleavage site (presence of multiple basic amino acids). Up until now, strict hygiene measures and regular controls are strongly recommended in farms in order to prevent avian flu, and in particular infection with the H5 and H7 subtypes.

In humans, immunization is recommended against the seasonal circulating viral strains responsible for epidemics that are more or less substantial according to the years. Most of the current vaccines are produced using embryonated hen eggs, these eggs being infected with three different flu virus strains (two strains of type A flu virus having the H3N2 and H1N1 subtype and one strain of type B virus). Eggs from hens that have not been immunized against the flu are used in order to prevent any phenomenon of interference which could be harmful to the replication of the virus. It is in fact known that the maternal antibodies are transferred to the chicks after having spent time in the egg and protect them against microbial infections during the first days of life, but, in return, they are responsible for deficient immunity if chicks are prematurely immunized against a microbial agent while protective maternal antibodies still exist against this agent. H. Stone et al. (1992, Avian Dis. 36: 1048-1051) have shown that newborn chicks can be passively immunized against Newcastle disease by inoculating yolk from eggs originating from hens immunized against the Newcastle disease virus (NDV). However, if, following the administration of the egg yolks, the chicks are immunized with the NDV virus, a decrease in the immune response to the vaccine is observed. It is also known, according to the studies by Hamal et al. (2006, Poultry Science 65: 1364-1372), that the rates of transfer of protective maternal antibodies to newborn chicks, in particular the transfer of antibodies directed against the NDV virus or the infectious bronchitis virus (IBV), is between 30% and 40% (percentage of the amount of antibodies in the hen's plasma circulating in the blood of the three-day-old chick), which indicates that a large amount of the maternal antibodies is sequestered in the egg. This is confirmed by the studies of J. R. Beck et al. (2003, Avian Dis. 47:1196-1199), which show that all the eggs contain anti-HA antibodies, approximately 3 weeks after having immunized hens with a strain of inactivated flu virus. Finally, it is known, according to the studies by Fontaine et al. (1963, Pathobiologie, 11/9: 611-613), that if embryonated eggs are inoculated with anti-flu serum, the eggs are protected against infection by the flu virus. All these reasons have led those skilled in the art to consider that if eggs from hens immunized against the flu were used, said eggs would, due to the transfer of the maternal antibodies directed against the flu into the eggs, become incapable of producing flu viruses.

Since the beginning of the 2000s, the economic consequence of avian flu in domestic bird farms has not ceased to increase with the appearance of highly contagious and pathogenic avian virus strains which decimate entire poultry farms. The typing of the HAs of highly pathogenic virus strains shows that almost all of them have the H5 or H7 subtype. It is now feared that virus strains having the H5 or H7 subtype will adapt to humans and may be responsible for a real flu pandemic in humans; serious cases of human flu, admittedly isolated, involving these subtypes have already been reported.

Faced with the risk that the supply of eggs may no longer always be ensured for manufacturing the flu vaccine, new methods of producing vaccines against the flu are currently directed toward the use of cell culture systems.

SUMMARY OF THE INVENTION

Despite new methods of producing vaccines, there still exists a need to be able to produce, under any circumstances, in a short period of time and in very large amount, flu virus for manufacturing the flu vaccine. The present invention meets this need by describing a method for producing flu virus based, against all expectations, on the use of eggs originating from hens immunized beforehand against the flu.

A subject of the invention is in fact:

A method for producing flu virus comprising:
a) immunizing a hen by administering a flu vaccine to the hen,
b) triggering embryogenesis in one or more eggs of the immunized hen,
c) infecting the one or more embryonated eggs by inoculating a flu virus into the allantoic cavity of the eggs,
d) incubating the one or more infected embryonated eggs under temperature and humidity conditions that allow replication of the virus, and
e) harvesting the allantoic fluid of the one or more incubated eggs containing the virus.

Preferably, the vaccine protects the hens against avian flu.

Typically, the flu vaccine comprises, in its composition, the hemagglutinin of a flu virus in the form of protein and/or of a gene encoding this protein.

According to one aspect, the composition of the flu vaccine contains an inactivated whole flu virus.

According to another aspect, the composition of the flu vaccine contains a product derived from a whole flu virus.

According to yet another aspect, the composition of the vaccine also contains an adjuvant.

In another aspect, the composition of the flu vaccine contains an attenuated flu virus.

According to another aspect, the flu vaccine comprises a vector comprising a nucleic acid fragment encoding the hemagglutinin of a flu virus.

According to another aspect, the composition of the vaccine also contains an adjuvant.

Preferably, the vector is a poxvirus.

In a specific aspect, the vector also comprises a nucleic acid fragment encoding the neuraminidase of a flu virus.

According to one embodiment of the method according to the invention, the flu virus hemagglutinin in the form of protein and/or of a gene encoding this protein contained in the composition of the vaccine which is used to immunize the hens against the flu and the hemagglutinin of the flu virus which is used to infect the allantoic cavity of the embryonated eggs from the immunized hens are of different subtypes.

According to another embodiment, the flu virus hemagglutinin in the form of protein and/or of a gene encoding this protein contained in the composition of the vaccine which is used to immunize the hens against the flu and the hemagglutinin of the flu virus which is used to infect the allantoic cavity of the embryonated eggs from the immunized hens are of the same subtype.

According to yet another embodiment, the flu virus hemagglutinin in the form of protein and/or of a gene encoding this protein contained in the composition of the vaccine which is used to immunize the hens against the flu and the hemagglutinin of the flu virus which is used to infect the allantoic cavity of the embryonated eggs from the immunized hens are identical.

According to yet another embodiment, the flu virus contained in the composition of the vaccine which is used to immunize the hens against the flu is identical to the flu virus which is used to infect the allantoic cavity of the embryonated eggs from the immunized hens.

In a particularly preferred embodiment, the flu virus hemagglutinin in the form of protein and/or of a gene encoding this protein contained in the composition of the vaccine which is used to immunize the hens against the flu and the hemagglutinin of the flu virus which is used to infect the allantoic cavity of the embryonated eggs from the immunized hens are independently selected from those of the H5, H6, H7 or H9 subtype.

In another particularly preferred embodiment, the flu virus hemagglutinin in the form of protein and/or of a gene encoding this protein contained in the composition of the vaccine which is used to immunize the hens against the flu and the hemagglutinin of the flu virus which is used to infect the allantoic cavity of the embryonated eggs from the immunized hens are independently of the H5 or H7 subtype.

In a specific aspect, the method according to the invention comprises an additional step of purification of the virus.

In another specific aspect, the method according to the invention comprises an additional step of inactivation of the virus.

The invention also comprises a flu vaccine obtained using a method according to the invention.

A subject of the invention is also the use of a method according to the invention for the manufacture of a vaccine for use in preventing the flu.

In a specific aspect, the use of the method according to the invention serves to manufacture a vaccine for use in preventing pandemic human flu.

In another specific aspect, the use of a method according to the invention serves to manufacture a vaccine for use in preventing epidemic human flu.

In yet another aspect, the use of a method according to the invention serves to manufacture a vaccine for use in preventing the flu in members of the equine family, members of the porcine family, members of the canine family, members of the feline family, mustelids and avian species.

A subject of the invention is also the use of the eggs from hens immunized against the flu for the production of a flu virus.

Finally, a subject of the invention is the use of the eggs from hens immunized against the flu for the manufacture of a flu vaccine.

In one aspect, the eggs from immunized hens contain antibodies against the hemagglutinin of flu virus.

In a further aspect, the eggs from immunized hens contain antibodies against H5, H6, H7 or H9 subtype.

All patents, patent applications, and publications referred to herein are hereby incorporated by reference.

BRIEF DESCRIPTION OF THE SEVERAL VIEWS OF THE DRAWING

FIG. 1. Represents the complete nucleotide sequence of the donor plasmid pJY1394.1; Seq. ID. No: 2.

FIG. 2. Represents the nucleotide sequence of the insert in the donor plasmid pJY1394.1, comprising the arms flanking the insertion locus F8, and also the H6 vaccinia promoter followed by the synthetic gene modified at the cleavage site encoding the HA of the A/chicken/Indonesia/7/03 strain; Seq. ID No: 3. Also depicted is the amino acid sequence of the HA; Seq. ID No: 1.

DETAILED DESCRIPTION OF THE INVENTION

The phrase "flu virus" denotes both flu virus originating from a wild-type strain and flu virus originating from a reassortant strain which results from the reassortment of the genomic segments of one or more wild-type strains with a "master" strain selected for its strong growth potential in eggs. The reassortant strain acquires characteristics of the "master" strain but keeps at least the characteristics of the HA and of the NA of the wild-type strain, which means that the identity of the protein structure of the HA and of the NA of the reassortant strain with respect to the HA and to the NA of the wild-type strain, determined by means of an overall alignment program, is at least 95%, preferably at least 98%, more preferably at least 99%, and even more preferably 100%. The reassortant strain can be obtained by coinfection of a sensitive cell with the wild-type strain and the "master" strain, followed by the appropriate means for selecting the desired reassortant strain. It can also be obtained by reverse genetics from the nucleic acids of the wild-type strain and of the "master" strain and expression in multiplasmid expression systems as described in WO 01/83794 and WO 03/091401 and in Proc. Nat. Acad. Sci. USA 96:9345-9350 (1999). In the case of the high path H5 and H7 strains, a modification of the cleavage site comprising the multiple basic amino acids may be carried out so as to render the reassortant strain low path.

For ease of language, the term "vaccinal strain" or "vaccinal virus" is used without distinction to denote the flu virus used for the manufacture of the flu vaccine; similarly, the term "infecting strain" or "infecting virus" is used to denote the flu virus used to infect biological material (eggs, animals).

Moreover, the term "eggs from immunized hens" is used to denote fertilized hen eggs originating from hens which have been immunized beforehand and brought into contact with roosters.

In general, the flu vaccine used for the immunization of the hens can be manufactured from any strain of flu virus. The vaccinal strain may be a type A virus, but also a type B or C virus. When it is a strain of type A virus, the virus may be any subtype of HA and/or any subtype of NA. It may, for example, be viral strains having the H1N1 or H3N2 subtype currently responsible for epidemic human type A flu.

There is a great advantage in immunizing hens with a flu virus provided that the immunization confers protection against avian flu.

Avian flu can pass unnoticed or can be characterized by a set of manifestations, often of respiratory and/or intestinal nature, of more or less great intensity, which more or less impair the general condition of the hens and which can result in the animal's death when the virus strain is highly pathogenic. Avian flu commonly results in a decrease or even a disappearance of the egg-laying activity. The low path virus strains belonging to the H6N2 or H9N2 or even H5 or H7 subtypes are commonly responsible for mild forms of avian flu, generally resulting in a decrease or a disappearance of egg production, but no great mortality. On the other hand, the high path virus strains belonging to the H5 and H7 subtypes (in particular H5N1, H5N2, H5N9, H7N1, H7N4 or H7N7) are highly virulent and cause a very high degree of mortality in hen farms.

HA is an antigen that is essential in the development of protective immunity against the flu. The vaccine used in the method according to the invention comprises in its composition at least the HA of a flu virus in the form of protein and/or of a gene encoding this protein.

The term "gene" is intended to mean a nucleic acid comprising nucleotide sequence corresponding to an open reading frame (ORF) and encoding a protein. The gene under the control of regulatory sequences for expression (promoter, enhancer, polyadenylation signal, transcription stop, etc.) can be inserted into the nucleic acid of a vector, in particular a plasmid or a virus. The regulatory sequences can be of exogen or endogen origin with respect to the ORF encoding the protein.

It may involve the HA of a human strain of flu virus but which is not pathogenic for hens. Preferably, it contains an HA of interest, i.e., an HA which has the same subtype as the HA of a viral strain which is responsible for an avian flu and against which it is sought to immunize and to protect the hens. Preferably, the degree of identity between the protein sequence of the HA present in the vaccine and that of the strain against which it is desired to protect the hens is at least 80%, preferably at least 90%, and even more preferably at least 95%, determined by means of an overall alignment program (such as the Blast program).

Conventionally, the vaccine comprising the HA is in the form of a composition containing inactivated whole flu virus, or a product derived from the inactivated whole flu virus.

The expression "product derived from an inactivated whole virus" is intended to mean an inactivated (i.e. noninfectious) vaccinal composition which is prepared from a strain of virus and which comprises at least the HA of said strain of virus. The product derived from a strain of whole virus may be fragmented (or split) virus and, in this case, reference is made to a "split" vaccine. Another product derived from a strain of whole virus is the HA of this strain as such or associated with the NA which has been obtained using extraction and purification methods and, in this case, reference is made to a "subunit" vaccine (EP 0 776 362). The HA may also be integrated secondarily into a virosome. The vaccinal composition containing inactivated whole flu virus, or a product derived from inactivated whole virus, may also contain one or more adjuvants or adjuvant formulations. As an example of nonlimiting adjuvant formulations, mention is made of water-in-oil or oil-in-water emulsions, such as the MF59 emulsion (Vaccine Design—The Subunit and Adjuvant Approach Edited by M. Powell and M. Newman, Plenum Press, 1995 page 183), liposome-based formulations, and formulations based on MPL (Vaccine Design—The Subunit and Adjuvant Approach Edited by M. Powell and M. Newman, Plenum Press, 1995 pages 1186-187), on avridine (Vaccine Design—The Subunit and Adjuvant Approach Edited by M. Powell and M. Newman, Plenum Press, 1995 page 148), on dimethyldioctadecylammonium bromide (Vaccine Design—The Subunit and Adjuvant Approach Edited by M. Powell and M. Newman, Plenum Press, 1995 page 157), on *Corynebacterium parvum*, on saponin, on lysolecithin, on pluronic derivatives (Hunter H. et al. 1991, vaccine, 9: 250-256) (Vaccine Design—The Subunit and Adjuvant Approach Edited by M. Powell and M. Newman, Plenum Press, 1995 page 200 and pages 297-311), on aluminum salts or on combinations thereof (Vaccine Design—The Subunit and Adjuvant Approach Edited by M. Powell and M. Newman, Plenum Press, 1995 pages 249-276). Preferably, the water-in-oil emulsions are composed of liquid paraffin, of a hydrophilic surfactant such as polysorbate 80 or polysorbate 85 and of a lipophilic surfactant such as sorbitan oleate or sorbitan trioleate. Examples of emulsions used in the hen are described in Stone et al. (1983, Avian Dis., 27: 688-697; 1993; Avian Dis., 37: 399-405; 1991, Avian Dis., 35: 8-16); in M. Brugh et al. (1983, Am. J; Vet. Res., 44: 72-75); in Woodward L. et al. (1985, Vaccine, 3: 137-144); in (Vaccine Design—The Subunit and Adjuvant Approach Edited by M. Powell and M. Newman, Plenum Press, 1995 page 219). The vaccinal strain generally originates from a wild-type strain which has been isolated in hens, turkeys, ducks, geese or in other avian species, this strain most commonly being low path for hens. As an example of isolates (wild-type strains) used for the preparation of vaccines for protecting hens against avian flu subtype H5 or H7, mention is made of the A/turkey/Wisconsin/68 or A/chicken/Italy/22A/98 isolates which are viral strains having the H5N9 subtype, the A/turkey/England/N-28/73, A/chicken/Mexico/238/94/CPA, A/chicken/Mexico/232/94/CPA or A/duck/Potsdam/1402/86 isolates which are viral strains having the H5N2 subtype, the A/goose/Guandong/1/1996 isolate which is an HP viral strain having the H5N1 subtype, the A/chicken/Italy/AG-473/1999 or A/chicken/Italy/1067/1999 isolates which are viral strains having the H7N1 subtype, the A/chicken/Pakistan/95 isolate which is an HP strain having the H7N3 subtype, and the A/duck/Potsdam/15/80 isolate which is a viral strain having the H7N7 subtype. As an example of H9N2 viral strains used for protecting domestic birds against avian flu subtype H9, mention is made of the A/chicken/Iran/AV12221/98 and A/chicken/UAE/415/99 isolates. As an example of an H6N2 viral strain used for protecting hens against avian flu subtype H6, mention is made of the A/turkey/Italy/90 isolate. The vaccinal strains used for the manufacture of vaccines may also be reassortants of wild-type strains obtained in particular by reverse genetics. Mention is in particular made of the Re-1 vaccinal strain which is a reassortant strain obtained by reverse recombination of the H5N1 wild-type strain A/goose/Guandong/1/96 with the "master" strain A/PR/8/34, which reproduces very well in eggs (Tian et al., 2005, Virology, 341:

153-162). Another example of a reassortant strain obtained by reverse genetics is the H5N3 strain obtained by genetic reassortment and containing the H5 hemagglutinin of the A/chicken/Vietnam/C58/04H5N1 strain, the neuraminidase of the A/duck/Germany/1215/73H2N3 strain and the internal genes of the A/PR/8/34 "master" strain (Webster et al., 2006, Virology, 351: 301-311).

The vaccines against avian flu usually contain the virus of a single inactivated flu virus strain (monovalent vaccines) but, in certain cases, it may be advantageous to use multivalent vaccines containing several inactivated flu virus strains. This is in particular a vaccine based on H7N1 and H5N9 strains which is a water-in-oil emulsion containing the inactivated vaccinal strains A/chicken/Italy/22A/98 (H5N9) and A/chicken/Italy/1067/1999 (H7N1). The inactivated vaccines may also contain different valences, for example a divalent vaccine against H9N2 avian flu and Newcastle disease. The inactivated vaccines are generally administered parenterally (intramuscularly or subcutaneously). They can also be administered in the form of a spray, as in the case of the Aerovac AI vaccine sold by Investigacion Aplicada, which contains the inactivated vaccinal strain A/chicken/Mexico/232/94/CPA (H5N2). The immunization scheme usually comprises one or two administrations 2 to 4 weeks apart. The vaccinal dose administered varies according to the age of the animals, but usually contains the equivalent of 10 to 200 μl of allantoic fluid having a titer of $10^8$ to $10^{10}$ $EID_{50}$/ml before inactivation. The vaccinal dose is usually administered in a volume ranging from 0.05 to 1 ml. The preparation of inactivated avian flu vaccines is described by H. Stone (1987, Avian Dis. 31: 483-490). Insofar as the vaccinal strain HA subtype is the same as that of the HA of the strain responsible for pathogenic avian flu, and on the basis of a degree of identity between the protein sequences of the two HAs of the order of 80% to 90%, determined by means of an overall alignment program, the protection rate obtained against the clinical symptoms of avian flu (morbidity and mortality) is generally more than 80%, and preferably more than 90%. This is confirmed by the studies of M. Bublot et al., 2007, Avian Dis. 51: 332-337, which show that a degree of identity of the order of 80% to 90% between the protein sequence of the vaccinal strain HA and the protein sequence of the pathogenic infecting strain HA is sufficient to obtain this protection rate. Furthermore, it is not necessary for the NA subtype of the vaccinal strain to be the same as that of the NA of the pathogenic infecting strain in order to obtain this protection rate. Moreover, the avian flu vaccines greatly reduce the excretion of the virus in immunized animals challenged with infectious virus, demonstrated by a very clear decrease in the viral load observed in oral and cloacal samples (M. Bublot et al., 2007, Avian Dis. 51: 332-337). Another beneficial effect of avian flu vaccines is that of reducing the diffusion of the virus in hen farms.

According to another embodiment of the method according to the invention, the vaccine used to immunize the hens is in the form of a composition comprising the virus originating from a live attenuated flu virus strain. The vaccinal strain is generally in the form of a reassortant which has been selected subsequent to genetic reassortment between a wild-type strain expressing the HA of interest and secondarily the NA of interest, and a "master" strain which has been cold-adapted and/or which is temperature-sensitive. The reassortant is a viral strain which expresses at its surface the HA and secondarily the NA of interest while at the same time retaining the phenotypic characteristics of the "master" strain which relate to its ability to replicate only within narrow temperature limits, below that of the internal temperature of birds. As a result, the vaccinal strain, after having been administered to hens, replicates in a limited manner and locally. The methods for obtaining these reassortant strains are well known to those skilled in the art and are described in particular in WO 03/091401 and WO 2006/063053 and in 2002, Vaccine 20: 2082-2090. The administration of the vaccine is generally carried out by nebulization. Another means of producing an attenuated strain is to truncate the gene encoding the NS1 protein (Richt J. A. et al., Vaccination of pigs against swine influenza viruses by using an NS1-truncated modified live-virus vaccine, 2006, J. Virol., 80: 11009-18; Quinlivan M. et al., Attenuation of equine influenza viruses through truncations of the NS1 protein, 2005, J. Virol., 79: 8431-9).

The vaccinal strains can be produced by any means, using culture techniques on cells such as Vero cells, MDCK cells, PER.C6 cells or chicken embryo cells (CEK, PCJ) and/or using conventional methods of production on embryonated eggs. The methods for harvesting, purifying and, as appropriate, inactivating the virus are also well known to those skilled in the art.

According to another embodiment of the method according to the invention, the vaccine is in the form of proteins produced in an in vitro expression system. For example, the HA can be produced in an expression system using a recombined baculovirus in insect cells (Crawford J. et al., Baculovirus-derived hemagglutinin vaccines protect against lethal influenza infections by avian H5 and H7 subtypes, 1999, Vaccine, 17: 2265-74). The hemagglutinin can also be expressed in vitro in the form of "virus-like particles" (VLPs) (Prel A. et al., Assessment of the protection afforded by triple baculovirus recombinant coexpressing H5, N3, M1 proteins against a homologous H5N3 low-pathogenicity avian influenza virus challenge in Muscovy ducks, 2007, Avian Dis., 51: 484-9; Pushko P. et al., Influenza virus-like particles comprised of the HA, NA, and M1 proteins of H9N2 influenza virus induce protective immune responses in BALB/c mice, 2005, Vaccine, 23: 5751-9) or of a retrovirus-based pseudotype (Szecsi J. et al., 2006, Virol. J., 3: 70). The proteins produced in vitro or the viral particles produced are more or less purified and then adjuvanted with various adjuvants, such as those used in inactivated vaccines.

According to another embodiment of the method according to the invention, the flu vaccine comprises a vector comprising a nucleic acid fragment encoding the flu virus HA.

The term "vector" refers to nucleic acid structures which can be propagated in and/or transferred into organisms, cells or cell components. This includes in particular plasmids, viruses, bacteriophages, proviruses, phagemids and artificial chromosomes which are capable of replicating autonomously or which can integrate into the chromosome of a host cell.

The expression "vector comprising a gene encoding the flu virus HA and/or NA" is intended to mean a vector containing the nucleic acid encoding the HA and/or NA of interest and which, after introduction into an avian cell, expresses the HA and/or NA in this cell. It may be a plasmid expressing the HA of interest, but it is generally a viral vector containing, in its genome, the nucleic acid encoding the HA of interest and expressing the HA of interest in the infected cells. The integration of the nucleic acid encoding the HA into the genome of the viral vector is generally carried out by molecular biology techniques, in particular genetic recombination, cloning, reverse genetics, etc. The HA may or may not be expressed at the surface of the viral vector. Preferably, the viral vector has been conventionally attenuated by multiple passages in vitro or by deletion of certain genes so that the replication of the vector virus in avian cells is sufficiently limited and has no effect on the general state of the hens and is thus considered to be nonpathogenic. As an example of viral vectors, mention is made of avian paramyxoviruses (Ge J., et al., Newcastle disease virus-based live attenuated vaccine completely protects chickens and mice from lethal challenge of homologous and heterologous H5N1 avian influenza viruses, 2007, J Virol., 81: 150-8); the turkey herpesvirus (HVT) or Marek's disease herpesvirus (Sondermeijer et al., 1993, Vaccine, 11, 349-358); the infectious laryngotracheitis virus (ILTV) (Veits J., et al., Deletion of the non-essential UL0 gene of infectious laryngotracheitis (ILT) virus leads to attenuation in chickens, and UL0 mutants expressing influenza virus haemagglutinin (H7) protect against ILT and fowl plague, 2003, J Gen. Virol., 84: 3343-52; Luschow D. et al., Protection of chickens from lethal avian influenza A virus infection by live-virus vaccination with infectious laryngotracheitis virus recombinants expressing the hemagglutinin (H5) gene, 2001, Vaccine, 19: 4249-59); adenoviruses (Francois A. et al., Avian adenovirus CELO recombinants expressing VP2 of infectious bursal disease virus induce protection against bursal disease in chickens, 2004, Vaccine, 22: 2351-60; Gao W. et al., Protection of mice and poultry from lethal H5N1 avian influenza virus through adenovirus-based immunization, 2006, J Virol., 80: 1959-64; Toro H. et al., Protective avian influenza in ovo vaccination with non-replicating human adenovirus vector, 2007, Vaccine, 25: 2886-91); coronaviruses (Cavanagh, 2007, Vet Res. 38: 281-97; Eriksson, 2006, Clin. Dev. Immunol. 13: 353-60), but use is preferably made, for immunizing hens, of poxviruses, in particular the vaccinia virus, NYVAC (deleted vaccinia virus), the vaccinia virus MVA strain, particularly avipoxes, especially canary pox, ALVAC (attenuated canary pox), pigeon pox, quail pox, turkey pox, sparrow pox and most particularly fowl pox, TROVAC (attenuated fowlpox), which are described in particular in AU 701599B and AU 701781B and in U.S. Pat. No. 5,756,103. As appropriate, the attenuated viral vectors express only the HA of interest: the vaccine involved is in particular the vaccine containing a TROVAC fowlpox vector expressing the HA of the H5N8 flu virus strain (A/turkey/Ireland/1378/83). In other cases, the attenuated viral vector expresses both the HA of interest in combination with an NA of interest, such as the recombinant poxvirus described in 2003, Avian Pathology, 32: 25-32, which expresses both the HA and the NA originating from an H5N1 flu virus strain. An NA of interest is an NA which has the same subtype as the NA of the viral strain against which it is sought to immunize and protect the hens. In yet other cases, the attenuated vector expresses several HAs of interest belonging to different subtypes, as in the case of the recombinant poxvirus described in 2006, Vaccine, 24: 4304-4311, which expresses both the H5 and H7 subtypes. The immunogenic capacity of these vectors can be further reinforced by introducing therein the genes encoding cytokines and/or chemokines which exert an immunostimulatory capacity, such as IL-1, IFN, CSF, GM-CSF, IL-2, IL-12, IL-18 or TNF 5 (2006, Vaccine, 24: 4304-4311). The vaccines based on vectors encoding the flu virus HA can also be adjuvanted in order to increase their immunogenicity.

The vaccinal compositions containing viral vectors can be administered by various routes, which depend in particular on the vector: for example, transfixion of the alar membrane (poxvirus vector), via the intramuscular, subcutaneous or transdermal route with or without needle (any vector), via the in ovo route (in the 17- to 19-day embryonated egg; for example, HVT/Marek and adenovirus vector), via the ocular or oronasal route, by spray, or in the drinking water (paramyxovirus, coronavirus, adenovirus vector), in one or two injections at least 15 days apart. The vaccinal dose(s) administered is (are) of the order of 1 to 7 $\log_{10}$ 50% infectious unit with a preference for a dose of 2 to 4 $\log_{10}$ for fowlpox vectors. The advantage of an immunization based on a viral vector compared with a conventional immunization using inactivated or attenuated whole flu virus lies in the fact that the immunized animals can be distinguished from the infected animals. Furthermore, immunization with a viral vector promotes the development of a cellular immunity that can reinforce the protection of the animals. As is illustrated in 2007, Avian Dis., 51: 325-331 and 2007, Avian Dis., 51: 498-500, the degree of protection obtained in the hens and the decrease in diffusion of the virus in poultry farms are of the same order as that which is observed with a conventional vaccine containing inactivated flu virus.

When the immunization of the hens comprises several injections, the vaccine used in the first administration may be different than that used in the second injection or the subsequent injections. Two different attenuated viral vectors may be used, for instance using a recombinant ALVAC vector expressing the HA of interest in the first immunization and a recombinant TROVAC or NYVAC vector expressing the same HA of interest in subsequent immunizations such that the antibody response directed against the ALVAC vector does not prevent the infection of the hen cells by the recombinant TROVAC or NYVAC vector and, consequently, the expression of the HA in the infected cells. It is also possible to use the "prime boost" method, which consists in using, in the first injection, an attenuated viral vector expressing an HA and in using, in the boost injection(s), a vaccine containing for example one or more inactivated vaccinal strains belonging to the same subtype as the HA used in the first immunization, or alternatively carrying out the process in reverse order. Finally, it is possible to carry out a DNA immunization in the first injection, using a plasmid expressing the HA of interest, followed by boost injections using a vaccine containing an inactivated vaccinal strain and/or an attenuated viral vector which express an HA belonging to the same subtype as the HA used in the first immunization or which is identical to the HA used in the first immunization.

Whatever the type of vaccine administered or the immunization scheme adopted, the protection of the hens against avian flu is provided quite rapidly, generally within a period of 7 to 18 days after the administration of a vaccinal dose. However, in order to ensure protection of the hens against avian flu throughout their egg-laying activity, which lasts approximately one year, one or two booster immunizations, which are carried out within a period of 3 to 16 weeks after the first vaccinal administration, are recommended. Several immunization schemes with inactivated vaccines can be used in egg-laying hens: for example, 2 injections, the first at 3 to 6 weeks old and the second at 16 to 19 weeks old, just before beginning egg laying, or 3 injections, the first around 2 to 4 weeks, the second 3 to 4 weeks later and the third at 16 to 19 weeks old just before beginning egg laying. A booster can also be administered during egg laying. In the "prime-boost" scheme using 2 different vaccines, the chicks can be immunized at 1 day old with a fowlpox vector-based vaccine; they subsequently receive one (at 16 to 19 weeks old just before beginning egg laying) or two (at 3 to 6 weeks old and at 16 to 19 weeks old just before beginning egg laying) immunizations with a vaccine containing inactivated flu virus.

In the implementation of the method according to the invention, the eggs are preferably taken from the hens once the protection of the hens against avian flu is ensured, which usually occurs within a period of 7 to 18 days after the administration of the vaccine (Bublot M. et al. (2006, Annals of the New York Academy of Sciences 1081: 193-201); Van der Goot et al. (2005, Proc. Natl. Acad. Sc., 102: 18141-6); Ellis et al. (Avian Pathol. 2004, 33, 405-412)).

Despite the presence of flu antibodies in the eggs of immunized hens, especially of antibodies directed against HA, and in particular of antibodies inhibiting hemagglutination (IHA) which block the penetration of the flu virus into sensitive cells, the method used for producing flu virus from embryonated eggs originating from hens immunized against the flu is conventional. 9- to 14-day embryonated eggs, originating from immunized hens which have been reared preferably in a controlled environment, are used. The embryogenesis process is controlled in the following way: eggs which have been conserved at a temperature between 10 and 20° C., preferably between 16 and 18° C., for a period which does not in general exceed one week after laying, are used. The embryogenesis process is triggered by incubating the eggs at a temperature of 37.5° C.±1° C. in a humid chamber having a relative humidity of 70±10% for a period of between 9 and 14 days. The embryonated eggs are selected by candling, and their allantoic cavities are infected with a dose of virus generally between 2 and 7 $\log_{10}$ $TCID_{50}$ in a small volume (approximately 0.1 to 0.2 ml). The virus is allowed to multiply for a period generally ranging from 1 to 4 days depending on the virulence of the viral strain, and at a temperature which can also vary according to the phenotype of the virus strain and its degree of cold- or hot-adaptation. The temperature for multiplication of the flu virus is generally in a range of from 28 to 39° C. and normally in a temperature range of from 33 to 39° C. The infectious allantoic fluids are then harvested and processed according to the uses intended to be made thereof.

This method can be used to produce a flu virus whose HA subtype is different than the subtype of the HA contained in the vaccine which was used to immunize the hens. This is, for example, the case where the hens are immunized with an inactivated H5N9 virus in order to protect the hens against H5 avian flu, while the eggs from these hens are infected with an H1N1 or H3N2 flu virus, or even a type B flu virus in order to prepare a vaccine against the epidemic forms of current human flu. According to a variant of the method according to the invention, the HA subtype of the flu virus which is produced using the embryonated eggs from immunized hens has a subtype that is different than the HA which was used to immunize the hens, but, on the other hand, the NA of the flu virus produced has the same subtype as the NA of the virus used in the vaccine. This is, for example, the case where the hens are immunized with an inactivated H5N1 virus strain or a recombinant poxvirus expressing H5 and N1 in order to protect the hens against avian flu, while the embryonated eggs from the immunized hens are infected with an H1N1 virus strain.

According to another mode of the method according to the invention, the HA of the flu virus produced on embryonated eggs from immunized hens has the same subtype as the HA contained in the vaccine which was used to immunize the hens. This is, for example, the case where the hens are immunized with inactivated H5N1 virus or a recombinant poxvirus expressing H5, while the eggs from the immunized hens are infected with an H5N1 or H5N9 flu virus. Despite the presence of "subtype"-specific crossreactive anti-HA antibodies in the egg (this is the case when the HA contained in the vaccinal composition has the same subtype as the HA of the flu virus strain infecting the embryonated eggs from immunized hens), this has no negative effect on the replication of the virus.

Furthermore, even more surprisingly, this replication is also not affected in the case where there is complete identity between the flu virus which was used to infect the embryonated eggs from immunized hens and the flu virus which was used to immunize these hens. In this case, this is reflected by the presence in the eggs of a panel of anti-HA antibodies which is even broader since both subtype-specific crossreactive anti-HA antibodies and anti-HA antibodies that are highly specific for the strain (also called strain-specific antibodies) are found (see example 3). Contrary to widely established opinion, the presence of flu antibodies in the egg and, in particular, the presence of anti-HA antibodies does not therefore affect the replication of the flu virus. The amounts of virus and/or of hemagglutinating antigen harvested in the infected allantoic fluids originating from eggs from hens immunized against the flu are of the same order as those harvested in infected allantoic fluids originating from eggs from nonimmunized hens (see examples 1 and 2).

The method according to the invention can also be taken advantage of for manufacturing a reassortant virus strain. In this case, in a first step, embryonated eggs from immunized hens are coinfected with a wild-type virus strain and a master virus strain which replicates well in embryonated eggs, for instance the A/PR/8/34 strain. In a second step, the infected allantoic fluids containing essentially a mixture of reassortants and the master strain, while the wild-type strain which is not as capable of replicating is generally in very small amount, are collected. The reassortant strain expressing at the same time the phenotypic characteristics of the A/PR/8/34 strain (i.e., its good ability to replicate in embryonated eggs) and the HA and also the NA of the wild-type strain is then selected with successive cloning steps by mixing at each cloning step the harvested infectious allantoic fluid with anti-HA and anti-NA antibodies specific for A/PR/8/34 according to methods well known to those skilled in the art. It is also possible to manufacture a cold-adapted and heat-sensitive reassortant strain with a view to a live attenuated virus vaccine. In this case, in a first step, embryonated eggs from immunized hens are coinfected with a wild-type virus strain and a master strain which has the phenotypic characteristic of being cold-adapted and heat-sensitive. In this case, the temperature for incubation of the infected eggs is a temperature that is lower than normal (the temperature is commonly below 35° C., or even below 30° C.). In a second step, the infected allantoic fluids containing essentially a mixture of reassortants and the master strain, since the cold-sensitive wild-type strain has not replicated, are collected. The reassortant expressing at the same time the phenotypic characteristics of the master strain (in particular the cold-adaptation and/or its thermosensitivity) and the HA and also the NA of the wild-type strain is then selected with successive cloning steps by mixing at each cloning step the harvested infectious allantoic fluid with anti-HA and anti-NA antibodies specific for the master strain according to methods well known to those skilled in the art.

The method according to the invention can be carried out as first line for preparing vaccines intended to protect breeding colonies of hens and more generally breeding colonies of domestic birds (ducks, turkeys, geese, etc.) against avian flu. The viral strains implicated in the asymptomatic or mild forms of avian flu may be of any subtype, and in particular the H9N2, H6N2, H7N2, H7N3 or H7N1 subtypes. They do not cause any substantial mortality in the breeding colonies but may be the cause of a transient decrease in egg production. The high path viral strains implicated in the serious forms of avian flu which cause substantial mortality in breeding colonies belong generally to the H5 and H7 subtypes, and in particular H5N1, H5N2, H5N8, H5N9, H7N1, H7N3, H7N4 or H7N7.

Generally, the flu virus hemagglutinin contained in the vaccinal composition which is used to immunize the hens against avian flu of the method according to the invention and the hemagglutinin of the virus which is used to infect the embryonated eggs of the method have the same subtype and are selected in particular from the H5, H6, H7 and H9 subtypes, since it is those which are found principally in the strains of virus responsible for avian flu.

In a specific aspect, the flu virus hemagglutinin contained in the vaccinal composition which is used to immunize the hens against avian flu of the method according to the invention and the hemagglutinin of the virus which is used to infect the embryonated eggs of the method have the same subtype and are selected from the H5 and H7 subtypes, since it is those which are found in the strains of virus responsible for the serious forms of avian flu and of human flu. The strains of virus responsible for the serious forms of avian flu and/or of human flu which have been characterized generally belong to the H5N1, H5N2, H7N1, H7N3 or H7N7 subtypes.

Thus, very specifically, a subject of the invention is:

A method for producing the flu virus comprising:
a) immunizing a hen with an inactivated flu virus, wherein the hemagglutinin of the virus has the H5 or H7 subtype,
b) triggering embryogenesis in one or more eggs of the immunized hen,
c) infecting the one or more embryonated eggs by introducing into the allantoic cavity of the embryonated eggs a flu virus identical to that that used for the immunization,
d) incubating the one or more infected embryonated eggs under temperature and humidity conditions that allow replication of the virus, and
e) harvesting the allantoic fluid containing the virus of the one or more incubated eggs.

When the immunization scheme of the hens comprises two injections, the first injection may be made with a vaccine composition wherein the inactivated flu virus is replaced by a vector, preferably a poxvirus comprising a gene encoding the H5 or H7 subtype of hemagglutinin.

When the infected allantoic fluids are intended for the production of a flu vaccine, the method according to the invention generally comprises an additional step of purifying the virus strain and is optionally followed or preceded by a viral inactivation step using methods well known to those skilled in the art such as those described in FR 2201079 or in FR 1538322.

The purification may be brief and may be limited to a step of concentrating the virus by centrifugation after having generally clarified the infected allantoic fluids. The purification may be supplemented with a zonal centrifugation step carried out for example by means of sucrose density gradients (EP 0 7760362). Chromatographic methods may also be carried out in order to purify the virus. A suspension of purified whole viruses which go to make up the composition of the inactivated whole vaccines or of attenuated vaccines is thus obtained.

The inactivation of the viral suspension can be carried out by conventional means, using β-propiolactone (E. Budowsky et al. 1991, Vaccine, 9: 319-325; 1991, Vaccine, 9: 398-402; 1993, Vaccine, 11: 343-348), ethyleneimine or derivatives (D. King 1991, Avian Dis. 35: 505-514) or formol (EP 0 776 0362).

The vaccinal composition based on inactivated whole viruses can be formulated with one or more adjuvants. Although conventionally these vaccines may be formulated with aluminum salts or in a water-in-oil or oil-in-water emulsion (in the case of avian flu vaccines), a water-in-oil emulsion composed of liquid paraffin, of a hydrophilic surfactant such as polysorbate 80, polysorbate 83 or polysorbate 85 and of a lipophilic surfactant such as sorbitan oleate, sorbitan sesquioleate or sorbitan trioleate is normally used. Any adjuvant capable of increasing the humoral and/or cellular response against the flu may be used. As an example of nonlimiting adjuvant formulations, mention is made of the MF59® emulsion, the liposome-based formulations, and formulations based on MPL, on *Corynebacterium parvum*, on saponin, on lysolecithin, on pluronic derivatives, or on combinations thereof.

The purified virus suspension may also undergo subsequent treatments and "flu virus-derived products" produced. For example the viral suspension may be fragmented using detergents or lipid solvents according using methods well known to those skilled in the art in order to manufacture, for example, vaccines based on fragmented or split viruses, virosomes, or subunit vaccines containing the flu virus hemagglutinin. Fragmented or split viruses, virosomes that contain the hemagglutinin of the flu virus, or subunit vaccines containing the flu virus hemagglutinin derived from the purified flu virus suspension are considered as "flu virus-derived products." These flu virus-derived products may similarly be formulated with one or more adjuvants.

The vaccines obtained by means of the method according to the invention are for use in protecting humans and animals against the flu.

In the veterinary field, the vaccine can be mainly used in the avian flu prevention field, but it may also be used for preventing or reducing flu symptoms and/or viral secretion in members of the equine family, in particular horses, members of the canine family, in particular dogs, members of the feline family, in particular cats, members of the porcine family, in particular pigs, mustelids, in particular minks and ferrets, and avian species, in particular hen, duck, turkey, quail, guineafowl, goose and ostrich. When the vaccinal composition contains an inactivated whole virus strain or a derived product, it is generally administered subcutaneously or intramuscularly, or optionally in the form of nebulized material in poultry breeding colonies. When the vaccine is in the form of a live attenuated virus, it is generally administered oronasally, by spray, in the drinking water or as a drop in the eye. The immunization scheme generally provides for an injection or an injection followed by a booster. The vaccinal dose administered depends on the size and the age of the animal. It usually contains between 20 and 200 µl of allantoic fluid having a titer of $10^8$ to $10^{10}$ $EID_{50}$/ml before inactivation, injected in a volume of between 0.05 and 1 ml.

In humans, the vaccine can be used in the field of epidemic flu and pandemic flu prevention. While epidemic flu affects a human population already sensitized by contact (by infection) or by immunization with one (or more) strain(s) of flu virus for which there exists an antigenic relationship with the HA of the virus strain responsible for the epidemic and in which there exists a certain immunity, even if it is only partially effective, pandemic flu affects a human population not sensitized to a new strain of virus because the HA of this new strain has no or too little an antigenic relationship with the prior circulating virus strains.

The epidemic flu vaccine is intended to protect the human population against seasonal flu forms brought about by circulating seasonal flu virus strains that have an antigenic relationship with prior virus strains that have already circulated. Currently, the flu virus strains responsible for epidemic flu, also called epidemic flu strains are of type A and belong to the H1N1 or H3N2 subtypes or are of type B.

The pandemic flu vaccine is intended to prevent the infection of the human population against a pandemic flu strain, which is a flu virus strain that has no antigenic relationship in terms of the HA with prior circulating flu virus strains.

The epidemic or pandemic flu vaccine may be in the form of a live attenuated vaccine or an inactivated vaccine, although an inactivated vaccine is preferred for the prevention of pandemic flu. The vaccine may be in the form of a monovalent vaccine (vaccine prepared from a single flu virus strain) or of a multivalent vaccine (vaccine prepared from several flu virus strains). The composition of the epidemic flu vaccine is currently in the form of a trivalent vaccine prepared from the H3N2 and H1N1 strains and from a type B virus strain. The inactivated vaccine is generally in the form of whole virus, of fragmented virus (split virus) or of virosomes, or in a subunit form containing HA, and optionally contains one or more adjuvants such as those mentioned above. While the live attenuated vaccine is generally administered orally or nasally in order to promote the development of mucosal immunity, the inactivated vaccine can be administered parenterally (intramuscularly or subcutaneously), intradermally or even mucosally (intranasally), or even by combining two different routes of administration as described in WO 01/22992. The immunization scheme generally provides for an injection or an injection followed by a booster. The vaccinal dose administered depends on the age of the individual and on the presence or absence of an adjuvant. Conventionally, the vaccinal dose contains the equivalent of 15 µg of HA of each vaccinal strain contained in the vaccine. This dose may be reduced to approximately 1 to 2 µg of HA when the vaccine is adjuvanted, or increased to 30 µg of HA or even more in elderly individuals or individuals suffering from an immune deficiency.

Finally, a subject of the invention also comprises:

The use of eggs from hens immunized against the flu, for the production of flu viruses or for the manufacture of a flu vaccine.

The following examples illustrate in a nonlimiting manner various embodiments of the invention.

FIG. 1 represents the complete nucleotide sequence of the donor plasmid pJY1394.1.

FIG. 2 represents the nucleotide sequence of the insert in the donor plasmid pJY1394.1 comprising the arms flanking the insertion locus F8, and also the H6 vaccinia promoter followed by the synthetic gene modified at the cleavage site encoding the HA of the A/chicken/Indonesia/7/03 strain.

The various origins of these sequences are the following:
From 1 to 53: partial sequence of the cloning plasmid comprising the sequence of the M13F primer (underlined).
From 54 to 1483: sequence of the "left arm" flanking the F8 insertion locus in the genome of the TROVAC fowlpox vector.
From 1484 to 1568: linker sequence between the left arm and the H6 promoter.
From 1569 to 1692: sequence of the vaccinia virus H6 promoter.
From 1693 to 3387: sequence of the modified synthetic HA gene of the A/chicken/Indonesia/7/03 strain; the amino acid sequence is indicated above the nucleotide sequence using the 1-letter code per amino acid.
From 3388 to 3414: linker sequence between the HA gene and the right arm comprising a TTTTTAT transcription stop sequence of the fowlpox early genes.
From 3415 to 4790: sequence of the "right arm" flanking the F8 insertion locus in the genome of the TROVAC fowlpox vector.
From 4791 to 4885: partial sequence of the cloning plasmid comprising the sequence of the M13R primer (underlined).

EXAMPLE 1

Method for Producing Two Vaccinal Strains A/New Caledonia/20/99 (H1N1) and A/New York/55/04 (H3N2) used to Prepare Vaccines Against Human Epidemic Flu Using Embryonated Eggs from Hens which have been Immunized, Either with Two Injections of an Inactivated Vaccine Containing an Avian Flu Virus Strain A/Chicken/Italy/22A/98 (H5N9), or by an Injection of a Recombinant Avipoxvirus Encoding the HA of an H5N1 Strain Followed by a Second Injection of an Inactivated Vaccine Containing an Avian Flu Virus Strain A/Chicken/Italy/22A/98 (H5N9)

1.1) Operating Protocol 1.1.1) Construction of the Recombinant Vector vFP2211 vFP2211 is a recombinant fowlpox virus, into the genome of which has been inserted a synthetic gene encoding the hemagglutinin (HA) of the A/chicken/Indonesia/7/03H5N1 strain. The HA gene was synthesized so as to obtain an open reading frame which encodes an amino acid sequence identical to the native sequence of the A/chicken/Indonesia/7/03 strain described in the GenBank nucleotide sequence database under the reference EF473080 (or the GenPept protein sequence database under the reference ABO30346), with the exception of the cleavage site. The RERRRKKRG amino acid sequence located between positions 339 and 347 (corresponding to the cleavage site of a high path strain) was replaced with the RE—TRG sequence. This cleavage site thus modified corresponds to the cleavage site of the low path strains of subtype H5.

In a first step, a donor plasmid pJY1394.1 comprising the modified synthetic HA gene under the control of the H6 vaccinia promoter (Taylor J. et al., Vaccine, 1988, 6: 504-508; Guo P. et al., J. Virol., 1989, 63: 4189-4198; Perkus M. et al., J. Virol., 1989, 63: 3829-3836) and bordered by the flanking arms of the F8 insertion locus so as to allow insertion of the HA gene into the F8 insertion locus of the fowlpox vector genome, was constructed. The F8 insertion locus corresponds to the fowlpox gene encoding photolyase described by Srinivasan and Tripathy (2005, Veterinary Microbiology 108: 215-223); this gene is also described under the name FPV158 in the complete sequence of the fowlpox genome (GenBank, reference AF198100). The insertion of the HA gene and of the H6 promoter into the F8 locus results in the deletion of the FPV158 gene from the recombinant fowlpox virus genome. The complete nucleotide sequence of the plasmid pJY1394.1 and also the series of nucleotide sequences bordering the HA gene (which also appear in the complete sequence of the plasmid) are described respectively in FIGS. 1 and 2.

The recombinant virus vFP2211 was then obtained by double recombination between the flanking arms of the plasmid pJY1394.1 and the fowlpox genome. For this, primary chicken embryo cells were transfected with the plasmid pJY1394.1 linearized with NotI and infected (multiplicity of infection of 10) with the parental fowlpox strain (TROVAC vector). The TROVAC vector derives from the vaccinal strain of the Diftosec vaccine produced by Merial against fowlpox in chickens. The recombinant viruses were selected by specific hybridization on lysis plaques with a probe for detecting the inserted HA gene. The vFP2211 thus isolated was then produced in rolling bottles on chicken embryo cells.

1.1.2) Preparation of the Inactivated H5N9 Vaccine

The inactivated H5N9 vaccine consisting of the low path A/chicken/Italy/22A/98 H5N9 strain (provided by the laboratory of Ilaria Capua (Istituto Zooprofilattico Sperimentale delle Venezie, Laboratorio Virologia, Padua, Italy)), which was produced on embryonated eggs and inactivated with beta-propiolactone (BPL), and of a water-in-oil emulsion composed of liquid paraffin, of sorbitan oleate and of polysorbate 80, was prepared according to a method equivalent to that described by H. Stone (1987, Avian Dis. 31: 483-490). The HLB (lipophilic hydrophilic balance) of the mixture of surfactants of the emulsion has a value of 5.3. A vaccinal dose is equivalent to 60 μl of allantoic fluid having a titer of $10^{8.9}$ $EID_{50}$/ml before inactivation.

1.1.3) Immunization of Egg-laying Hens

Two groups (G1 and G2) of 1-day (D0) Leghorn chicks, having the "specific pathogen free" (SPF) status, were formed. The following immunization scheme was applied to group G1: the 1-day (D0) chicks received subcutaneously, at the base of the neck, using an insulin syringe, 0.2 ml of a viral suspension of vFP2211 having a titer of $3.0 \log_{10} CCID_{50}/0.2$ ml. At the age of 8 weeks (W8) the chickens were sexed. Approximately 25 pullets and 16 roosters were conserved and put together. At the age of 17 weeks (W17) they received a booster injection of a vaccinal dose in a volume of 0.5 ml of the monovalent inactivated H5N9 vaccine.

The following immunization scheme was applied to group G2: the 3-week-old SPF chicks received, by IM injection, in the wishbone, using an insulin syringe, a vaccinal dose in a volume of 0.3 ml of the monovalent inactivated H5N9 vaccine. At the age of 8 weeks (W8), the chickens were sexed. Approximately 25 pullets and 16 roosters were conserved and put together. At the age of 17 weeks (W17) they received a booster injection of a vaccinal dose in a volume of 0.5 ml of the monovalent inactivated H5N9 vaccine.

1.1.4) Protocol for Infection of Eggs Originating from the Hens of Groups G1 and G2 and from Nonimmunized Hens, with the A/New Caledonia/20/99 IVR-116 (H1N1) or A/New York/55/04 X-157 (H3N2) Virus Strains The ability of the reassortant vaccinal strains A/New Caledonia/20/99 (xPR8) called A/New Caledonia/20/99 IVR-116 (H1N1) and A/New York/55/04 (xPR8) called A/New York/55/04 X-157 (H3N2) to replicate was evaluated in the eggs from the hens of group G1 which were laid at 40-41 (test 2) and 49-50 (test 3) weeks of age and in the eggs from the hens of group G2 which were laid at 26-27 (test 1), 40-41 (test 2) and 49-50 (test 3) weeks of age. In parallel, the ability of the virus strains A/New Caledonia/20/99 (xPR8) (H1N1) and A/New York/55/04 (xPR8) (H3N2) to replicate was evaluated in the same manner in the control eggs derived from nonimmunized SPF hens (control group).

All the eggs laid during the week were conserved in a temperature-controlled chamber (12 to 15° C.). The eggs of the same test and originating from the same group of animals were grouped together and then the embryogenesis process was triggered by incubating the eggs for 10 days at 37-38° C. in a chamber in which the relative humidity was approximately 70-80%. After incubation for 10 days, the vitality of the embryo was verified in each egg by means of a candling device, and the allantoic cavity was pinpointed with a cross. The embryonated eggs of the same test and originating from the same group of animals were grouped together in pools of 8 eggs. The embryonated eggs of the same pool were infected with the same infectious dose of flu virus injected in a volume of 200 μl at the level of the cross after having disinfected and then pierced the shell of the egg. Infectious doses of $10^2$, $10^3$ and $10^4$ $EID_{50}$ (egg infectious dose 50%) of A/New Caledonia/20/99 (xPR8) (H1N1) and A/New York/55/04 (xPR8) (H3N2) virus were tested. Infectious doses of $10^3$ and $10^4$ $EID_{50}$ per egg were tested in the eggs of tests 1 and 2. Infectious doses of $10^2$ and $10^3$ $EID_{50}$ per egg were tested in the eggs of test 3. The infected embryonated eggs were then incubated at 34° C. for 48 hours in a chamber in which the relative humidity was 80%, and then placed at +4° C. overnight. The infected allantoic fluid was then taken from each egg. The infecting titer was evaluated on each allantoic fluid taken by measuring the HAU (hemagglutinating unit) titer. Turkey red blood cells were used to measure the HAU titers of the allantoic fluids infected with the A/New York/55/04 (xPR8) (H3N2) strain. Hen red blood cells were used to measure the HAU titers of the allantoic fluids infected with A/New Caledonia/20/99 (xPR8) (H1N1). The HAU titer was expressed by the inverse of the last dilution of the infected allantoic fluid which showed visible hemagglutination in the presence of a suspension of hen or turkey red blood cells at 0.5% in phosphate buffer.

1.2) Results

The means of the HAU titers obtained in the eggs originating from the various groups of immunized and nonimmunized hens as a function of the infectious dose of virus injected into the eggs and as a function of the time at which the eggs were sampled are given in tables I and II.

TABLE I

Hemagglutinating titers obtained in the allantoic fluids as a function of the infecting dose of A/New Caledonia/20/99 (xPR8) (H1N1) used, of the origin of the eggs (G1, G2, nonimmunized control) and of the moment at which the eggs were laid (test 1, test 2, test 3).

| | Infecting dose ($EID_{50}$/egg) | | | | | |
|---|---|---|---|---|---|---|
| | 100 | 1000 | | | 10 000 | |
| Group | test 3 | test 1 | test 2 | test 3 | test 1 | test 2 |
| Nonimmunized control | 640* | 1050 | 1660 | 1280 | 861 | 1522 |
| G1 (vFP2211/Vac. Inact. H5N9) | 1140 | NA | 1974 | 830 | NA | 1974 |
| G2 (Vac. Inact. H5N9/Vac. Inact. H5N9) | 806 | 905 | 1660 | 1159 | 905 | 1974 |

*Hemagglutinating titer (HAU) expressed in the form of the geometric mean of 8 HAU titers/50 μl obtained on the allantoic fluids of the 8 eggs included in each condition.
NA: Not applicable

TABLE II

Hemagglutinating titers obtained in the allantoic fluids as a function of the infecting dose of A/New York/55/04 (xPR8) (H3N2) used, of the origin of the eggs (G1, G2, nonimmunized control) and of the time at which the eggs were laid (test 1, test 2, test 3)

| | Infecting dose ($EID_{50}$/egg) | | | |
|---|---|---|---|---|
| | 100 | 1000 | | 10 000 |
| Group | test 3 | test 1 | test 3 | test 1 |
| Nonimmunized control | 211* | 861 | 349 | 830 |
| G1 (vFP2211/Vac. Inact. H5N9) | 88 | NA | 254 | NA |

TABLE II-continued

Hemagglutinating titers obtained in the allantoic fluids as a function of the infecting dose of A/New York/55/04 (xPR8) (H3N2) used, of the origin of the eggs (G1, G2, nonimmunized control) and of the time at which the eggs were laid (test 1, test 2, test 3)

| | Infecting dose (EID$_{50}$/egg) | | | |
|---|---|---|---|---|
| | 100 | 1000 | | 10 000 |
| Group | test 3 | test 1 | test 3 | test 1 |
| G2 (Vac. Inact. H5N9/Vac. Inact. H5N9) | 254 | 987 | 557 | 844 |

*Hemagglutinating titer (HAU) expressed in the form of the geometric mean of 8 HAU titers/50 µl obtained on the allantoic fluids of the 8 eggs included in each condition.
NA: Not applicable The results obtained in tables I and II show that the means of the HAU titers of the allantoic fluids of the eggs originating from immunized hens (G1 and G2) are equivalent to the means of the HAU titers of the allantoic fluids of the eggs originating from nonimmunized hens.

A statistical analysis was carried out in order to study the immunization and dose factors. The individual values of the HAUs were converted to log$_2$ and then analyzed using a model of variance. The variance heterogeneity was tested using the test for reduced size, performed with the residues of the model (SAS v8.2 software).

The statistical analysis carried out on the individual values of the HAU titers showed that there was no immunization effect. Neither was there any effect related to the dose of virus which was used to infect the eggs. The HAU titers did not substantially fluctuate during the egg-laying period studied (ranging from 26 weeks (test 1) to 50 weeks (test 3)).

EXAMPLE 2

Method for Producing Two Pandemic Vaccinal Strains A/Chicken/Italy/22A/98 (H5N9) and A/Vietnam/1194/04 NIBRG14 (H5N1) Using Embryonated Eggs from Hens which have been Immunized, Either with Two Injections of an Inactivated Vaccine Containing an Avian Flu Virus Strain A/Chicken/Italy/22A/98 (H5N9), or with an Injection of a Recombinant Avipoxvirus Encoding the HA of an H5N1 Strain Followed by a Second Injection of an Inactivated H5N9 Vaccine Containing an Avian Flu Virus Strain 2.1.1) Immunization of Hens The protocol for immunizing the hens was identical to that which was used in example 1.

2.1.2) Protocol for Infection of Eggs Originating from the Hens of Groups G1 and G2 and from Nonimmunized Hens, with the A/Chicken/Italy/22A/98 (H5N9) and A/Vietnam/1194/04 NIBRG14 (H5N1) Virus Strains The infection protocol was the same as that which was used in example 1, except for the following modifications:

The low path A/Chicken/Italy/22A/98 (H5N9) avian strain originating from the Laboratoire Istituto Zooprofilattico Sperimentale delle Venezie, Laboratorio Virologia, Padua, Italy and an attenuated pandemic reassortant vaccinal strain A/Vietnam/1194/04 NIBRG14 (H5N1) were used to infect the eggs. The latter strain was provided by the National Institute for Biological Standards and Control (NIBSC) laboratory, South Mimms, Potters Bar, Herts EN6 3QG, UK and was obtained by reverse genetics, as is described by C. Nicolson et al., Generation of influenza vaccine viruses on Vero cells by reverse genetics: an H5N1 candidate vaccine strain produced under a quality system, 2005, Vaccine, 23: 2943-2952.

Infectious doses of $10^2$, $10^3$, $10^4$ and $10^5$ EID$_{50}$ (egg infectious dose 50%) were tested for these two strains. Infectious doses of $10^3$, $10^4$ and $10^5$ EID$_{50}$ per egg were tested in the eggs of test 1. Infectious doses of $10^4$ and $10^5$ EID$_{50}$ per egg were tested in the eggs of test 2. Infectious doses of $10^2$ and $10^3$ EID$_{50}$ per egg were tested in the eggs of test 3.

Hen red blood cells were used to measure the HAU titers of the allantoic fluids infected with A/chicken/Italy/22A/98 (H5N9) or A/Vietnam/1194/04 NIBRG14 (H5N1).

2.2) Results

The HAU titers obtained in the eggs originating from the various groups of immunized and nonimmunized hens, as a function of the infectious dose of virus injected into the eggs and as a function of the time at which the eggs were taken, are given in tables III and IV.

TABLE III

Hemagglutinating titers obtained in the allantoic fluids as a function of the infecting dose of A/chicken/Italy/22A/98 (H5N9) used, of the origin of the eggs (G1, G2, nonimmunized control) and of the time at which the eggs were laid (test 1, test 2, test 3)

| | Infecting dose (EID$_{50}$/egg) | | | | | | |
|---|---|---|---|---|---|---|---|
| | 100 | 1000 | | 10 000 | | 100 000 | |
| Group | test 3 | test 1 | test 3 | test 1 | test 2 | test 1 | test 2 |
| Nonimmunized control | 35* | 53 | 32 | 53 | 64 | 54 | 53 |
| G1 (vFP2211/Vac. Inact. H5N9) | 64 | NA | 54 | NA | 59 | NA | 86 |
| G2 (Vac. Inact. H5N9/Vac. Inact. H5N9) | 102 | 64 | 57 | 59 | 70 | 102 | 59 |

*Hemagglutinating titer (HAU) expressed in the form of the geometric mean of 8 HAU titers/50 µl obtained on the allantoic fluids of the 8 eggs included in each condition.
NA: Not applicable

TABLE IV

Hemagglutinating titers obtained in the allantoic fluids as a function of the infecting dose of A/Vietnam/1194/04 (H5N1) RG14 used, of the origin of the eggs (G1, G2, nonimmunized control) and of the time at which the eggs were laid (test 1, test 2, test 3)

| | Infecting dose (EID$_{50}$/egg) | | | | |
|---|---|---|---|---|---|
| | 1000 | 10 000 | | 100 000 | |
| Group | test 1 | test 1 | test 2 | test 1 | test 2 |
| Nonimmunized control | 194* | 232 | 197 | 172 | 181 |
| G1 (vFP2211/Vac. Inact. H5N9) | NA | NA | 197 | NA | 166 |
| G2 (Vac. Inact. H5N9/Vac. Inact. H5N9) | 152 | 279 | 215 | 181 | 235 |

*Hemagglutinating titer (HAU) expressed in the form of the geometric mean of 8 HAU titers/50 µl obtained on the allantoic fluids of the 8 eggs included in each condition.
NA: Not applicable The results given in tables III and IV and also the statistical analysis show that the HAU titers of the allantoic fluids originating from the eggs from the immunized hens (G1 and G2) are similar to the HAU titers of the allantoic fluids of the eggs from the nonimmunized hens, even in the situation where the hens were immunized with a strain identical to that which was used to infect the embryonated eggs originating from these hens (in the case of groups G1 and G2 immunized with the A/chicken/Italy/22A/98 (H5N9) strain). There is no effect, either, related to the dose of virus which is used to infect the eggs. The HAU titers did not substantially fluctuate during the egg-laying period studied (ranging from 26 weeks (test 1) to 50 weeks (test 3)).

The statistical analysis was carried out as in example 1.

EXAMPLE 3

Analysis of the Anti-H5 Maternal Antibody Response in the Eggs from Hens which have been Immunized with the A/Chicken/Italy/22A/98 (H5N9) Vaccinal Strain 3.1) Operating Protocol The presence of anti-H5 antibodies in the eggs from the hens of groups G1 and G2 which were immunized with the A/chicken/Italy/22A/98 (H5N9) strain was measured according to the protocol described in paragraph 1.1.1). In parallel, the anti-H5 response was also analyzed in the yolks of eggs from nonimmunized hens (control group).

The anti-H5 response was analyzed in the yolks of eggs (or vitelline fluids) which were taken at the time of tests 1 (W26-27), 2 (W40-41) and 3 (W49-50). The analysis of the anti-H5 response in the yolks of eggs of test 1 was carried out before embryogenesis (D0) and after embryogenesis (D10) (i.e. after the phase of incubation for 10 days at 37° C.). The analysis of the anti-H5 responses in the yolks of eggs of tests 2 and 3 was carried out only after embryogenesis (D10). The same analysis was also carried out with eggs originating from nonimmunized hens (see paragraph 3.2.2)). The anti-H5 response was also studied in the allantoic fluids of the eggs of test 2 after embryogenesis (D10). The egg yolks were removed by suction using a pipette with a disposable tip. With the exception of test 1, where the egg yolks were kept frozen without having been prediluted, the egg yolks of tests 2 and 3 and the allantoic fluids were prediluted to ⅕th in phosphate buffer before freezing. The diluted egg yolks and the allantoic fluids were conserved frozen until the time of the anti-H5 antibody assay which was carried out using the method of assaying by inhibition of hemagglutination (IHA) of hen red blood cells which takes place in the presence of the A/chicken/Italy/22A/98 (H5N9) strain. The assay was based on the ability of the neutralizing antibodies directed specifically against the HA of the virus to inhibit the "hemagglutinating" activity of the virus. In this test, anti-A/Vietnam/1194/04 sheep serum provided by the NISBC was used as positive control and naïve mouse serum was used as negative control. Successive two-fold dilutions of the samples (diluted egg yolks or allantoic fluids) were carried out in a conical-bottomed microplate in order to obtain 50 µl of each of the dilutions per well. 50 µl of a viral suspension having a titer of 4 hemagglutinating units (4HAU) and originating from a clarified allantoic fluid which was infected with the A/chicken/Italy/22A/98 (H5N9) strain provided by the laboratory of Ilaria Capua (Istituto Zooprofilattico Sperimentale delle Venezie, Laboratorio Virologia, Padua, Italy), were added to each well. This was left to incubate for 1 hour at laboratory temperature before adding 50 µl of a solution of hen red blood cells at 0.5% in phosphate buffer. After leaving to stand for 1 hour at +4° C., the test was read. The presence of inhibition of hemagglutination was reflected by the presence of a red spot at the bottom of the microwell, while the presence of hemagglutination was reflected by the presence of a pinkish halo in the microwell. The IHA antibody titer was represented by the inverse of the last dilution where no hemagglutination is observed in the microwell.

3.2) Results 3.2.1) Analysis of the Anti-H5 Response in the Egg Yolks of Test 1

At D0, 8 of the 8 egg yolks analyzed of the nonimmunized group were negative in the IHA test, whereas 6 of the 8 egg yolks originating from group 2 were positive in the IHA test, which indicated the presence of anti-H5 antibodies.

At D10, 4 of the 4 egg yolks analyzed of the nonimmunized group were negative in the IHA test, whereas 4 of the 4 egg yolks originating from group 2 were positive in the IHA test.

3.2.2) Analysis of the Anti-H5 Response in the Egg Yolks and the Allantoic Fluids of Test 2

At D10, 5 of the 5 egg yolks analyzed of the nonimmunized group were negative in the IHA test, whereas 4 of the 5 egg yolks originating from group 1, and 4 of the 5 egg yolks originating from group 2, were positive in the IHA test, which indicated the existence of anti-H5 antibodies in these groups. The individual values of the IHA titers obtained are given in table V.

TABLE V

| IHA titers for the yolks of eggs taken after embryogenesis (D10) | |
|---|---|
| Egg yolks | D10* |
| Group 1 | 160 |
| (vFR2211/Vac. Inact. H5N9) | 80 |
|  | 320 |
|  | 80 |
|  | <5 |
| Group 2 | 80 |
| (Vac. Inact. H5N9/Vac. Inact. | 160 |
| H5N9) | 40 |
|  | 40 |
|  | <5 |
| Nonimmunized group | <5 |
|  | <5 |
|  | <5 |
|  | <5 |
|  | <5 |

*The titers at D10 originate from different egg yolks

On the other hand, all the allantoic fluids originating from groups 1 and 2 were negative in the IHA test, which means that there were no antibodies inhibiting the hemagglutination of the H5N9 flu virus that were detectable in the allantoic fluids.

3.2.3) Analysis of the Anti-H5 Response in the Egg Yolks of Test 3

At D10, 5 of the 5 egg yolks analyzed of the nonimmunized group were negative in the IHA test, whereas 5 of the 5 egg yolks originating from group 1 were positive in the IHA test.

The individual values of the IHA titers are given in table VI.

TABLE VI

IHA titers of the yolks of eggs taken after embryogenesis (D10) as a function of the origin of the eggs

| Egg yolks | D10 |
|---|---|
| Group 1 | 80 |
| (vFP2211/Vac. Inact. H5N9) | 80 |
|  | 160 |
|  | 5 |
|  | 320 |
| Nonimmunized group | <5 |
|  | <5 |
|  | <5 |
|  | <5 |
|  | <5 |

In conclusion, on the basis of the results of examples 2 and 3, the presence of maternal anti-H5N9 antibodies, which was revealed in the egg yolks of the 3 tests, has no effect on the viral productivity of the allantoic fluids infected with an H5N1 or H5N9 strain.

EXAMPLE 4

Analysis of the Serological Response of Hens Immunized with the A/Chicken/Italy/22A/98 (H5N9) Vaccinal Strain and of the Maternal Anti-H5 Antibodies Present in the Eggs from these Immunized Hens Blood samples were taken, at 28 and 36 weeks of age, from the immunized hens of groups 1 and 2. The eggs laid by these hens were collected at weeks 27 and 37 in order to evaluate the importance of the transfer of the maternal antibodies into the egg yolks. The anti-H5 antibody response was evaluated by means of the hemagglutination inhibition test using as antigen the A/chicken/Italy/22A/98H5N9 strain homologous to the inactivated vaccine strain. The results are expressed as $\log_{10}$ in table VII.

TABLE VII

Hemagglutination-inhibiting antibody titers (A/chicken/Italy/22A/98 H5N9 antigen) in the serum of immunized egg-laying hens and in the vitellus of the eggs laid by these hens

|  | Serum | Vitellus | Serum | Vitellus |
|---|---|---|---|---|
| Weeks of age | 28 | 27 | 36 | 37 |
| G1 | 2.10 ± 0.61 (15)* | 1.96 ± 0.94 (21)** | 1.92 ± 0.91 (15) | 1.63 ± 0.89 (10) |
| G2 | 2.20 ± 0.62 (15) | 1.81 ± 0.88 (13) | 2.26 ± 0.65 (15) | 1.43 ± 0.89 (14) |

*geometric mean of the hemagglutination-inhibiting antibody titers, expressed as $\log_{10}$ ± standard deviation (number of samples tested per group)
**the lowest dilution tested on the vitelli is 1/10 (1 $\log_{10}$); for the calculation of the means and standard deviation, the values of the eggs that were negative at the 1/10 dilution were placed at 0.7 $\log_{10}$.

TABLE VIII

Hemagglutination-inhibiting antibody titers (A/turkey/Wisconsin/68 H5N9 antigen) in the vitellus of the eggs laid by the immunized hens of groups 1 and 2

|  | Vitellus |
|---|---|
| Weeks of age | 27 |
| G1 | 1.67 ± 0.79 (21)* |
| G2 | 1.39 ± 0.80 (13) |

*geometric mean of the hemagglutination-inhibiting antibody titers, expressed as $\log_{10}$ ± standard deviation (number of samples tested per group); the lowest dilution tested is 1/10 (1 $\log_{10}$); for the calculation of the means and standard deviation, the values of the eggs that were negative at the 1/10 dilution were placed at 0.7 $\log_{10}$.

These results confirm the transmission of the maternal antibodies into the egg yolks of the eggs laid by the immunized hens of groups 1 and 2.

The homologous anti-H5N9 antibody titers (table VII) in the vitellus are greater than the heterologous anti-H5N9 titers (table VIII), although this difference is not statistically significant.

EXAMPLE 5

Production of the A/Turkey/Wisconsin/68H5N9 Strain on Eggs Laid by Hens Immunized with an Inactivated H5N9 Vaccine (A/Chicken/Italy/22A/98 Strain) of Group 2

5.1. Operating Protocol

The eggs (approximately 220-230) from the hens of group 2 immunized twice at 3 and 17 weeks of age with the inactivated H5N9 vaccine (A/chicken/Italy/22A/98 strain) were taken during weeks 28 and 29. These eggs, after storage at controlled temperature (between 12 and 15° C.), were incubated at 37° C. for 11 days. After candling in order to verify that the embryos had good viability, the eggs were inoculated in the allantoic cavity with 0.2 ml of a dilution of a stock viral solution of the A/turkey/Wisconsin/68 H5N9 strain having a titer of 9.68 $\log_{10}$ $EID_{50}$/ml (inoculum). Seven groups of approximately 30 eggs were formed. Four groups (G1 to G4) were inoculated with the following dilutions of the inoculum: $10^{-5}$, $10^{-4}$, $10^{-3}$ and $10^{-2}$. Three other groups (G5 to G7) were inoculated with the $10^{-3}$ dilution of the inoculum. After inoculation, the eggs were incubated at 37° C.±1.5° C. in 70%±10% humidity. After incubation for 20 h, the eggs were candled in order to eliminate the dead eggs derived from the inoculation and they were then reincubated under the same conditions. Forty-two hours after the inoculation, the eggs were placed in the cold before harvesting the allantoic fluid. The allantoic fluids of the eggs of groups 1 to 4 were pooled (one pool of fluid per group). The allantoic fluids of the 4 groups of eggs were stored at −70° C. before being titered in terms of hemagglutinating units and of egg infectious dose 50% ($EID_{50}$).

5.2. Results

The results are given in table IX.

TABLE IX

Hemagglutinating and infectious titers obtained after production of the A/turkey/Wisconsin/68 H5N9 strain on eggs originating from hens immunized with an inactivated vaccine containing the A/chicken/Italy/22A/98 H5N9 strain

| Group | Inoculum dilution | Titer in hemagglutinating units ($\log_{10}$) | Infectious titer $EID_{50}$ ($\log_{10}$/ml) |
|---|---|---|---|
| 1 | $10^{-5}$ | 2.25 | 9.50 |
| 2 | $10^{-4}$ | 2.40 | 9.33 |
| 3 | $10^{-3}$ | 2.25 | 9.67 |
| 4 | $10^{-2}$ | 2.40 | 9.88 |

These results show very similar titers between the groups and there is therefore no effect of the dilution of the inoculum. Furthermore, the titers obtained are very high and are comparable to those obtained on eggs having no maternal anti-H5N9 antibodies (historical laboratory data). These results therefore confirm that, under the conditions tested, the presence of maternal antibodies in the eggs does not interfere with the production of a flu virus of the same subtype.

What is claimed is:

1. A method for producing flu virus comprising:
   a) immunizing a hen by administering a flu vaccine to the hen,
   b) triggering embryogenesis in one or more eggs of the immunized hen,
   c) infecting the one or more embryonated eggs by inoculating a flu virus into the allantoic cavity of the eggs,
   d) incubating the one or more infected embryonated eggs under temperature and humidity conditions that allow replication of the virus, and
   e) harvesting the allantoic fluid of the one or more incubated eggs containing the virus.

2. The method as claimed in claim 1, wherein the flu vaccine comprises hemagglutinin of a flu virus in the form of protein and/or of a gene encoding this protein.

3. The method as claimed in claim 2, wherein the flu vaccine protects the hen against avian flu.

4. The method as claimed in claim 2, wherein the flu vaccine comprises an inactivated whole flu virus or a live attenuated flu virus.

5. The method as claimed in claim 2, wherein the flu vaccine comprises a product derived from an inactivated whole flu virus.

6. The method as claimed in claim 2, wherein the vaccine also comprises an adjuvant.

7. The method as claimed in claim 2, wherein the flu vaccine comprises a vector comprising a gene encoding flu virus hemagglutinin.

8. The method as claimed in claim 7, wherein the vector is a poxvirus.

9. The method as claimed in claim 8, wherein the vector also comprises a gene encoding flu virus neuraminidase.

10. The method as claimed in claim 7, wherein the vaccine also comprises an adjuvant.

11. The method as claimed in claim 2, wherein the flu virus hemagglutinin in the form of protein and/or of a gene encoding this protein contained in the composition of the vaccine that is administered to the hens and the hemagglutinin of the flu virus that is used to infect the allantoic cavity of the embryonated eggs from the immunized hens are of different subtypes.

12. The method as claimed in claim 2, wherein the flu virus hemagglutinin in the form of protein and/or of a gene encoding this protein contained in the composition of the vaccine that is administered to the hens and the hemagglutinin of the flu virus that is used to infect the allantoic cavity of the embryonated eggs from the immunized hens are of the same subtype.

13. The method as claimed in claim 2, wherein the flu virus hemagglutinin in the form of protein and/or of a gene encoding this protein contained in the composition of the vaccine that is administered to the hens and the hemagglutinin of the flu virus that is used to infect the allantoic cavity of the embryonated eggs from the immunized hens are identical.

14. The method as claimed in claim 4, wherein the flu virus contained in the composition of the vaccine that is administered to the hens is identical to the flu virus that is used to infect the allantoic cavity of the embryonated eggs from the immunized hens.

15. The method as claimed in claim 2, wherein the flu virus hemagglutinin in the form of protein and/or of a gene encoding this protein contained in the composition of the vaccine that is administered to the hens and the hemagglutinin of the flu virus that is used to infect the allantoic cavity of the embryonated eggs from the immunized hens are independently selected from the group of hemagglutinins of the H5, H6, H7 and H9 subtypes.

16. The method as claimed in claim 15, wherein the flu virus hemagglutinin in the form of protein and/or of a gene encoding this protein contained in the composition of the vaccine that is administered to the hens and the hemagglutinin of the flu virus that is used to infect the allantoic cavity of the embryonated eggs from the immunized hens are of the same subtype.

17. The method as claimed in claim 16, wherein the flu virus hemagglutinin in the form of protein and/or of a gene encoding this protein contained in the composition of the vaccine that is administered to the hens and the hemagglutinin of the flu virus that is used to infect the allantoic cavity of the embryonated eggs from the immunized hens are identical.

18. The method as claimed in claim 1, wherein the method further comprises purification of the virus.

19. The method as claimed in claim 18, wherein the method further comprises inactivation of the virus.

* * * * *

UNITED STATES PATENT AND TRADEMARK OFFICE
CERTIFICATE OF CORRECTION

| | |
|---|---|
| PATENT NO. | : 7,871,807 B2 |
| APPLICATION NO. | : 12/238740 |
| DATED | : January 18, 2011 |
| INVENTOR(S) | : Gerdil et al. |

It is certified that error appears in the above-identified patent and that said Letters Patent is hereby corrected as shown below:

Title page should read;
(73) Sanofi Pasteur S.A., Lyon (FR); Merial Limited, Duluth, GA (US)

Signed and Sealed this
Fifth Day of April, 2011

David J. Kappos
*Director of the United States Patent and Trademark Office*

```
SEQUENCE LISTING

<160> NUMBER OF SEQ ID NOS: 3

<210> SEQ ID NO 1
<211> LENGTH: 564
<212> TYPE: PRT
<213> ORGANISM: Avian influenza virus
<220> FEATURE:
<221> NAME/KEY: Sequence of the HA protein of the
      A/chicken/Indonesia/7/03 avian flu virus
<222> LOCATION: (1)..(564)
<223> OTHER INFORMATION: Amino acid sequence encoded by the modified
      synthetic HA gene at the level of the cleavage site

<400> SEQUENCE: 1

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Leu Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Lys Ser Ser Phe Phe
145                 150                 155                 160

Arg Asn Val Val Trp Leu Ile Lys Lys Asn Ser Ala Tyr Pro Thr Ile
                165                 170                 175

Lys Arg Ser Tyr Asn Asn Thr Asn Gln Glu Asp Leu Leu Val Leu Trp
            180                 185                 190
```

```
Gly Ile His His Pro Asn Asp Ala Ala Glu Gln Thr Arg Leu Tyr Gln
            195                 200                 205

Asn Pro Thr Thr Tyr Ile Ser Val Gly Thr Ser Thr Leu Asn Gln Arg
        210                 215                 220

Leu Val Pro Lys Ile Ala Ile Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
370                 375                 380

Lys Ala Ile Asp Gly Val Thr Asn Lys Val Asn Ser Ile Ile Asp Lys
385                 390                 395                 400

Met Asn Thr Gln Phe Glu Ala Val Gly Arg Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Ile Arg Asn
                485                 490                 495

Gly Thr Tyr Asn Tyr Pro Gln Tyr Ser Glu Glu Ala Arg Leu Lys Arg
            500                 505                 510

Glu Glu Ile Ser Gly Val Lys Leu Glu Ser Ile Gly Thr Tyr Gln Ile
        515                 520                 525

Leu Ser Ile Tyr Ser Thr Val Ala Ser Ser Leu Ala Leu Ala Ile Met
530                 535                 540

Met Ala Gly Leu Ser Leu Trp Met Cys Ser Asn Gly Ser Leu Gln Cys
545                 550                 555                 560

Arg Ile Cys Ile

<210> SEQ ID NO 2
<211> LENGTH: 7618
<212> TYPE: DNA
<213> ORGANISM: Artificial
<220> FEATURE:
<223> OTHER INFORMATION: donor plasmid pYJ1394.1
```

<400> SEQUENCE: 2

```
ctaaattgta agcgttaata ttttgttaaa attcgcgtta aattttttgtt aaatcagctc    60
atttttttaac caataggccg aaatcggcaa aatcccttat aaatcaaaag aatagaccga   120
gataggggttg agtgttgttc cagtttggaa caagagtcca ctattaaaga acgtggactc   180
caacgtcaaa gggcgaaaaa ccgtctatca gggcgatggc ccactacgtg aaccatcacc   240
ctaatcaagt ttttttggggt cgaggtgccg taaagcacta aatcggaacc ctaaagggag   300
cccccgattt agagcttgac ggggaaagcc ggcgaacgtg gcgagaaagg aagggaagaa   360
agcgaaagga gcgggcgcta gggcgctggc aagtgtagcg gtcacgctgc gcgtaaccac   420
cacacccgcc gcgcttaatg cgccgctaca gggcgcgtcc cattcgccat tcaggctgcg   480
caactgttgg gaagggcgat cggtgcgggc ctcttcgcta ttacgccagc tggcgaaagg   540
gggatgtgct gcaaggcgat taagttgggt aacgccaggg ttttcccagt cacgacgttg   600
taaaacgacg gccagtgaat tgtaatacga ctcactatag ggcgaattgg gtgacccttt   660
acaagaataa aagaagaaac aactgtgaaa tagtttataa atgtaattcg tatgcagaaa   720
acgataatat attttggtat gagaaatcta aaggagacat agtttgtata gacatgcgct   780
cttccgatga gatattcgat gctttttctaa tgtatcatat agctacaaga tatgcctatc   840
atgatgatga tatatatcta caaatagtgt tatattattc taataatcaa aatgttatat   900
cttatattac gaaaaataaa tacgttaagt atataagaaa taaaactaga gacgatattc   960
ataaagtaaa aatattagct ctagaagact ttacaacgga agaaatatat tgttggatta  1020
gtaatatata acagcgtagc tgcacggttt tgatcatttt ccaacaatat aaaccaatga  1080
aggaggacga ctcatcaaac ataaataaca ttcacggaaa atattcagta tcagatttat  1140
cacaagatga ttatgttatt gaatgtatag acggatcttt tgattcgatc aagtatagag  1200
atataaaggt tataataatg aagaataacg gttacgttaa ttgtagtaaa ttatgtaaaa  1260
tgcggaataa atacttttct agatggttgc gtctttctac ttctaaagca ttattagaca  1320
tttacaataa taagtcagta gataatgcta ttgttaaagt ctatggtaaa ggtaagaaac  1380
ttattataac aggattttat ctcaaacaaa atatgatacg ttatgttatt gagtggatag  1440
gggatgattt tacaaacgat atatacaaaa tgattaattt ctataatgcg ttattcggta  1500
acgatgaatt aaaaatagta tcctgtgaaa acactctatg cccgtttata gaacttggta  1560
gatgctatta tggtaaaaaa tgtaagtata tacacggaga tcaatgtgat atctgtggtc  1620
tatatatact acaccctacc gatattaacc aacgagtttc tcacaagaaa acttgtttag  1680
tagatagaga ttctttgatt gtgtttaaaa gaagtaccag taaaaagtgt ggcatatgca  1740
tagaagaaat aaacaaaaaa catatttccg aacagtattt tggaattctc ccaagttgta  1800
aacatatttt ttgcctatca tgtataagac gttgggcaga tactaccaga aatacagata  1860
ctgaaaatac gtgtcctgaa tgtagaatag ttttttcctt cataatacccc agtaggtatt  1920
ggatagataa taaatatgat aaaaaaatat tatataatag atataagaaa atgattttta  1980
caaaaatacc tataagaaca ataaaaatat aattacattt acggaaaata gctggtttta  2040
gtttaccaac ttagagtaat tatcatattg aatctatatt gctaattagc taataaaaac  2100
ccgggttaat taattagtca tcaggcaggg cgagaacgag actatctgct cgttaattaa  2160
ttagagcttc tttattctat acttaaaaag tgaaaataaa tacaaaggtt cttgagggtt  2220
gtgttaaatt gaaagcgaga aataatcata aattatttca ttatcgcgat atccgttaag  2280
```

```
tttgtatcgt aatggagaaa atcgtgctgc tgctggccat cgtgagcctg gtgaaaagcg   2340
atcagatctg catcggctac cacgccaaca acagcacaga gcaagtggac acaatcatgg   2400
aaaagaacgt gaccgtgaca cacgcccagg acatcctgga aaagacacac aacgggaagc   2460
tgtgcgatct ggatggagtg aagcctctga tcctgagaga ttgcagcgtg gccggatggc   2520
tgctggggaa cccaatgtgc gacgaattca tcaacgtgcc cgaatggagc tacatcgtgg   2580
agaaggccaa cccagccaac gacctgtgct acccagggaa cctgaacgac tacgaagaac   2640
tgaaacacct gctgagcaga atcaaccact tgagaaaaat ccagatcatc cccaaaagca   2700
gctggtccga tcacgaagcc agcagcggag tgagcagcgc ctgcccatac cagggaaagt   2760
ccagcttttt tagaaacgtg gtgtggctga tcaaaaagaa cagcgcctac ccaacaatca   2820
agagaagcta caacaacacc aaccaggaag atctgctggt gctgtggggg atccaccacc   2880
ctaacgatgc cgccgagcag acaaggctgt accagaaccc aaccacctac atctccgtgg   2940
ggacaagcac actgaaccag agactggtgc caaaaatcgc catcagatcc aaagtgaacg   3000
ggcagagcgg aagaatggag ttcttctgga caatcctgaa acccaacgat gccatcaact   3060
tcgagagcaa cggaaacttc atcgccccag aatacgccta caaaatcgtg aagaaggggg   3120
acagcgccat catgaaaagc gaactggaat acggcaactg caacaccaag tgccagaccc   3180
caatgggggc catcaacagc agcatgccat tccacaacat ccaccctctg accatcgggg   3240
aatgccccaa atacgtgaaa agcaacagac tggtgctggc caccgggctg agaaacagcc   3300
ctcagagaga gaccgagaga ctgtttggag ccatcgccgg cttttatcga ggaggatggc   3360
agggaatggt ggatggctgg tacggatacc accacagcaa cgagcagggg agcggatacg   3420
ccgccgacaa agaatccacc cagaaggcca tcgacgcgt gaccaacaaa gtgaacagca   3480
tcatcgacaa aatgaacacc cagtttgagg ccgtgggaag ggagtttaac aacctggaaa   3540
ggagaatcga gaacctgaac aagaagatgg aggacggatt cctggatgtg tggacctaca   3600
acgccgaact gctggtgctg atggaaaacg agagaaccct ggactttcac gacagcaacg   3660
tgaagaacct gtacgacaaa gtgaggctgc agctgaggga taacgccaag gagctgggca   3720
acggctgctt cgagttctac cacaaatgcg ataacgaatg catggaaagc atcagaaacg   3780
gaacctacaa ctaccccag tacagcgaag aagccagact gaaaagagaa gaaatctccg   3840
gagtgaaact ggaatccatc ggaacctacc agatcctgag catctacagc acagtggcct   3900
cctccctggc cctggccatc atgatggccg gactgagcct gtggatgtgc tccaacggaa   3960
gcctgcagtg cagaatctgc atctgactcg agttttttatt gactagttaa tcataagata   4020
aataatatac agcattgtaa ccatcgtcat ccgttatacg gggaataata ttaccataca   4080
gtattattaa attttcttac gaagaatata gatcggtatt tatcgttagt ttatttttaca   4140
tttattaatt aaacatgtct actattacct gttatggaaa tgacaaattt agttatataa   4200
tttatgataa aattaagata ataataatga atcaaataa ttatgtaaat gctactagat   4260
tatgtgaatt acgaggaaga aagtttacga actggaaaaa attaagtgaa tctaaaatat   4320
tagtcgataa tgtaaaaaaa ataaatgata aaactaacca gttaaaaacg gatatgatta   4380
tatacgttaa ggatattgat cataaaggaa gagatacttg cggttactat gtacaccaag   4440
atctggtatc ttctatatca aattggatat ctccgttatt cgccgttaag gtaaataaaa   4500
ttattaacta ttatatatgt aatgaatatg atatacgact tagcgaaatg gaatctgata   4560
tgacagaagt aatagatgta gttgataaat tagtaggagg atacaatgat gaaatagcag   4620
aaataatata tttgtttaat aaatttatag aaaaatatat tgctaacata tcgttatcaa   4680
```

```
ctgaattatc tagtatatta ataattttta taaattttaa taaaaaatac aataacgaca   4740
taaaagatat taaatcttta attcttgatc tgaaaaacac atctataaaa ctagataaaa   4800
agttattcga taaagataat aatgaatcga acgatgaaaa attggaaaca gaagttgata   4860
agctaatttt tttcatctaa atagtattat tttattgaag tacgaagttt tacgttagat   4920
aaataataaa ggtcgatttt tattttgtta aatatcaaat atgtcattat ctgataaaga   4980
tacaaaaaca cacggtgatt atcaaccatc taacgaacag atattacaaa aaatacgtcg   5040
gactatggaa aacgaagctg atagcctcaa tagaagaagc attaaagaaa ttgttgtaga   5100
tgttatgaag aattgggatc atcctctcaa cgaagaaata gataaagttc taaactggaa   5160
aaatgataca ttaaacgatt tagatcatct aaatacagat gataatatta aggaaatcat   5220
acaatgtctg attagagaat ttgcgtttaa aaagatcaat tctattatgt atagttatgc   5280
tatggtaaaa ctcaattcag ataacgaaac attgaaagat aaaattaagg attattttat   5340
agaaactatt cttaaagaca aacgtggtta taaacaaaag ccattaccct agagcggccg   5400
ccaccgcggt ggagctccag cttttgttcc ctttagtgag ggttaatttc gagcttggcg   5460
taatcatggt catagctgtt tcctgtgtga aattgttatc cgctcacaat tccacacaac   5520
atacgagccg gaagcataaa gtgtaaagcc tggggtgcct aatgagtgag ctaactcaca   5580
ttaattgcgt tgcgctcact gcccgctttc cagtcgggaa acctgtcgtg ccagctgcat   5640
taatgaatcg gccaacgcgc ggggagaggc ggtttgcgta ttgggcgctc ttccgcttcc   5700
tcgctcactg actcgctgcg ctcggtcgtt cggctgcggc gagcggtatc agctcactca   5760
aaggcggtaa tacggttatc cacagaatca ggggataacg caggaaagaa catgtgagca   5820
aaaggccagc aaaaggccag gaaccgtaaa aaggccgcgt tgctggcgtt tttccatagg   5880
ctccgccccc ctgacgagca tcacaaaaat cgacgctcaa gtcagaggtg gcgaaacccg   5940
acaggactat aaagatacca ggcgtttccc cctggaagct ccctcgtgcg ctctcctgtt   6000
ccgaccctgc cgcttaccgg atacctgtcc gcctttctcc cttcgggaag cgtggcgctt   6060
tctcatagct cacgctgtag gtatctcagt tcggtgtagg tcgttcgctc caagctgggc   6120
tgtgtgcacg aaccccccgt tcagcccgac cgctgcgcct tatccggtaa ctatcgtctt   6180
gagtccaacc cggtaagaca cgacttatcg ccactggcag cagccactgg taacaggatt   6240
agcagagcga ggtatgtagg cggtgctaca gagttcttga agtggtggcc taactacggc   6300
tacactagaa ggacagtatt tggtatctgc gctctgctga agccagttac cttcggaaaa   6360
agagttggta gctcttgatc cggcaaacaa accaccgctg gtagcggtgg tttttttgtt   6420
tgcaagcagc agattacgcg cagaaaaaaa ggatctcaag aagatccttt gatcttttct   6480
acggggtctg acgctcagtg gaacgaaaac tcacgttaag ggattttggt catgagatta   6540
tcaaaaagga tcttcaccta gatccttttt aattaaaaat gaagttttaa atcaatctaa   6600
agtatatatg agtaaacttg gtctgacagt taccaatgct taatcagtga ggcacctatc   6660
tcagcgatct gtctatttcg ttcatccata gttgcctgac tccccgtcgt gtagataact   6720
acgatacggg agggcttacc atctggcccc agtgctgcaa tgataccgcg agacccacgc   6780
tcaccggctc cagatttatc agcaataaac cagccagccg gaagggccga gcgcagaagt   6840
ggtcctgcaa ctttatccgc ctccatccag tctattaatt gttgccggga agctagagta   6900
agtagttcgc cagttaatag tttgcgcaac gttgttgcca ttgctacagg catcgtggtg   6960
tcacgctcgt cgtttggtat ggcttcattc agctccggtt cccaacgatc aaggcgagtt   7020
```

-continued

```
acatgatccc ccatgttgtg caaaaaagcg gttagctcct tcggtcctcc gatcgttgtc    7080
agaagtaagt tggccgcagt gttatcactc atggttatgg cagcactgca taattctctt    7140
actgtcatgc catccgtaag atgcttttct gtgactggtg agtactcaac caagtcattc    7200
tgagaatagt gtatgcggcg accgagttgc tcttgcccgg cgtcaatacg ggataatacc    7260
gcgccacata gcagaacttt aaaagtgctc atcattggaa aacgttcttc ggggcgaaaa    7320
ctctcaagga tcttaccgct gttgagatcc agttcgatgt aacccactcg tgcacccaac    7380
tgatcttcag catcttttac tttcaccagc gtttctgggt gagcaaaaac aggaaggcaa    7440
aatgccgcaa aaaagggaat aagggcgaca cggaaatgtt gaatactcat actcttcctt    7500
tttcaatatt attgaagcat ttatcagggt tattgtctca tgagcggata catatttgaa    7560
tgtatttaga aaaataaaca aatagggggtt ccgcgcacat ttccccgaaa agtgccac     7618
```

<210> SEQ ID NO 3
<211> LENGTH: 4885
<212> TYPE: DNA
<213> ORGANISM: Artificial
<220> FEATURE:
<223> OTHER INFORMATION: nucleotide sequence of the insert of the
      plasmid pYJ1394.1
<220> FEATURE:
<221> NAME/KEY: partial sequence of the cloning plasmid comprising the
      sequence of the M13F primer
<222> LOCATION: (1)..(53)
<220> FEATURE:
<221> NAME/KEY: sequence of the "left arm" flanking the F8 insertion
      locus in the genome of the TROVAC fowlpox vector
<222> LOCATION: (54)..(1483)
<220> FEATURE:
<221> NAME/KEY: linker sequence between the left arm and the H6 promoter
<222> LOCATION: (1484)..(1568)
<220> FEATURE:
<221> NAME/KEY: sequence of the vaccinia virus H6 promoter
<222> LOCATION: (1569)..(1692)
<220> FEATURE:
<221> NAME/KEY: sequence of the modified synthetic HA gene of the A/chicken/Indonesia/7/03 strain
<222> LOCATION: (1693)..(3387)
<220> FEATURE:
<221> NAME/KEY: linker sequence between the HA gene and the right arm
<222> LOCATION: (3388)..(3414)
<223> OTHER INFORMATION: sequence comprising a TTTTTAT transcription stop sequence of the fowlpox early genes
<220> FEATURE:
<221> NAME/KEY: sequend of the “right arm” flanking the F8 insertion locus in the genome of the TROVAC folwpox vector
<222> LOCATION: (3415)..(4790)
<220> FEATURE:
<221> NAME/KEY: partial sequence of the cloning plasmid comprising the sequence of the M13R primer
<222> LOCATION: (4791)..(4885)

<400> SEQUENCE: 3

```
gtaaaacgac ggccagtgaa ttgtaatacg actcactata gggcgaattg ggtgaccctt     60
tacaagaata aaagaagaaa caactgtgaa atagtttata aatgtaattc gtatgcagaa    120
aacgataata tattttggta tgagaaatct aaaggagaca tagtttgtat agacatgcgc    180
tcttccgatg agatattcga tgcttttcta atgtatcata tagctacaag atatgcctat    240
catgatgatg atatatatct acaaatagtg ttatattatt ctaataatca aaatgttata    300
tcttatatta cgaaaaataa atacgttaag tatataagaa ataaaactag agacgatatt    360
cataaagtaa aaatattagc tctagaagac tttacaacgg aagaaatata ttgttggatt    420
agtaatatat aacagcgtag ctgcacggtt ttgatcattt tccaacaata taaaccaatg    480
aaggaggacg actcatcaaa cataaataac attcacggaa aatattcagt atcagattta    540
```

-continued

```
tcacaagatg attatgttat tgaatgtata gacggatctt ttgattcgat caagtataga    600
gatataaagg ttataataat gaagaataac ggttacgtta attgtagtaa attatgtaaa    660
atgcggaata aatactttc tagatggttg cgtctttcta cttctaaagc attattagac     720
atttacaata ataagtcagt agataatgct attgttaaag tctatggtaa aggtaagaaa    780
cttattataa caggatttta tctcaaacaa aatatgatac gttatgttat tgagtggata    840
ggggatgatt ttacaaacga tatatacaaa atgattaatt tctataatgc gttattcggt    900
aacgatgaat taaaaatagt atcctgtgaa aacactctat gcccgtttat agaacttggt    960
agatgctatt atggtaaaaa atgtaagtat atacacggag atcaatgtga tatctgtggt   1020
ctatatatac tacaccctac cgatattaac caacgagttt ctcacaagaa aacttgttta   1080
gtagatagag attctttgat tgtgtttaaa agaagtacca gtaaaaagtg tggcatatgc   1140
atagaagaaa taaacaaaaa acatatttcc gaacagtatt ttggaattct cccaagttgt   1200
aaacatattt tttgcctatc atgtataaga cgttgggcag atactaccag aaatacagat   1260
actgaaaata cgtgtcctga atgtagaata gttttttcctt tcataatacc cagtaggtat   1320
tggatagata ataaatatga taaaaaaata ttatataata gatataagaa aatgattttt   1380
acaaaaatac ctataagaac aataaaaata taattacatt tacggaaaat agctggtttt   1440
agtttaccaa cttagagtaa ttatcatatt gaatctatat tgctaattag ctaataaaaa   1500
cccgggttaa ttaattagtc atcaggcagg gcgagaacga gactatctgc tcgttaatta   1560
attagagctt ctttattcta tacttaaaaa gtgaaaataa atacaaaggt tcttgagggt   1620
tgtgttaaat tgaaagcgag aaataatcat aaattatttc attatcgcga tatccgttaa   1680
gtttgtatcg taatggagaa aatcgtgctg ctgctggcca tcgtgagcct ggtgaaaagc   1740
gatcagatct gcatcggcta ccacgccaac aacagcacag agcaagtgga cacaatcatg   1800
gaaaagaacg tgaccgtgac acacgcccag gacatcctgg aaaagacaca aacgggaag    1860
ctgtgcgatc tggatggagt gaagcctctg atcctgagag attgcagcgt ggccggatgg   1920
ctgctgggga acccaatgtg cgacgaattc atcaacgtgc cgaatggag ctacatcgtg    1980
gagaaggcca acccagccaa cgacctgtgc tacccaggga acctgaacga ctacgaagaa   2040
ctgaaacacc tgctgagcag aatcaaccac tttgagaaaa tccagatcat ccccaaaagc   2100
agctggtccg atcacgaagc cagcagcgga gtgagcagcg cctgcccata ccagggaaag   2160
tccagctttt ttagaaacgt ggtgtggctg atcaaaaaga acagcgccta cccaacaatc   2220
aagagaagct acaacaacac caaccaggaa gatctgctgg tgctgtgggg gatccaccac   2280
cctaacgatg ccgccgagca gacaaggctg taccagaacc caaccaccta catctccgtg   2340
gggacaagca cactgaacca gagactggtg ccaaaaatcg ccatcagatc caaagtgaac   2400
gggcagagcg gaagaatgga gttcttctgg acaatcctga aacccaacga tgccatcaac   2460
ttcgagagca acggaaactt catcgcccca gaatacgcct acaaaatcgt gaagaaaggg   2520
gacagcgcca tcatgaaaag cgaactggaa tacggcaact gcaacaccaa gtgccagacc   2580
ccaatggggg ccatcaacag cagcatgcca ttccacaaca tccaccctct gacccatcggg   2640
gaatgcccca aatacgtgaa aagcaacaga ctggtgctgg ccaccgggct gagaaacagc   2700
cctcagagag agaccagagg actgtttgga gccatcgccg gctttatcga gggaggatgg   2760
cagggaatgg tggatggctg gtacggatac caccacagca acgagcaggg gagcggatac   2820
gccgccgaca aagaatccac ccagaaggcc atcgacggcg tgaccaacaa agtgaacagc   2880
```

-continued

```
atcatcgaca aaatgaacac ccagtttgag gccgtgggaa gggagtttaa caacctggaa    2940
aggagaatcg agaacctgaa caagaagatg gaggacggat tcctggatgt gtggacctac    3000
aacgccgaac tgctggtgct gatggaaaac gagagaaccc tggactttca cgacagcaac    3060
gtgaagaacc tgtacgacaa agtgaggctg cagctgaggg ataacgccaa ggagctgggc    3120
aacggctgct tcgagttcta ccacaaatgc gataacgaat gcatggaaag catcagaaac    3180
ggaacctaca actacccca gtacagcgaa gaagccagac tgaaaagaga agaaatctcc    3240
ggagtgaaac tggaatccat cggaacctac cagatcctga gcatctacag cacagtggcc    3300
tcctccctgg ccctggccat catgatggcc ggactgagcc tgtggatgtg ctccaacgga    3360
agcctgcagt gcagaatctg catctgactc gagtttttat tgactagtta atcataagat    3420
aaataatata cagcattgta accatcgtca tccgttatac ggggaataat attaccatac    3480
agtattatta aattttctta cgaagaatat agatcggtat ttatcgttag tttattttac    3540
atttattaat taaacatgtc tactattacc tgttatggaa atgacaaatt tagttatata    3600
atttatgata aaattaagat aataataatg aaatcaaata attatgtaaa tgctactaga    3660
ttatgtgaat tacgaggaag aaagtttacg aactggaaaa aattaagtga atctaaaata    3720
ttagtcgata atgtaaaaaa aataaatgat aaaactaacc agttaaaaac ggatatgatt    3780
atatacgtta aggatattga tcataaagga agagatactt gcggttacta tgtacaccaa    3840
gatctggtat cttctatatc aaattggata tctccgttat tcgccgttaa ggtaaataaa    3900
attattaact attatatatg taatgaatat gatatacgac ttagcgaaat ggaatctgat    3960
atgacagaag taatagatgt agttgataaa ttagtaggag gatacaatga tgaaatagca    4020
gaaataatat atttgtttaa taaatttata gaaaaatata ttgctaacat atcgttatca    4080
actgaattat ctagtatatt aaataatttt ataaatttta ataaaaaata caataacgac    4140
ataaaagata ttaaatcttt aattcttgat ctgaaaaaca catctataaa actagataaa    4200
aagttattcg ataaagataa taatgaatcg aacgatgaaa aattggaaac agaagttgat    4260
aagctaattt ttttcatcta aatagtatta ttttattgaa gtacgaagtt ttacgttaga    4320
taaataataa aggtcgattt ttattttgtt aaatatcaaa tatgtcatta tctgataaag    4380
atacaaaaac acacggtgat tatcaaccat ctaacgaaca gatattacaa aaaatacgtc    4440
ggactatgga aaacgaagct gatagcctca atagaagaag cattaaagaa attgttgtag    4500
atgttatgaa gaattgggat catcctctca acgaagaaat agataaagtt ctaaactgga    4560
aaaatgatac attaaacgat ttagatcatc taaatacaga tgataatatt aaggaaatca    4620
tacaatgtct gattagagaa tttgcgttta aaaagatcaa ttctattatg tatagttatg    4680
ctatggtaaa actcaattca gataacgaaa cattgaaaga taaaattaag gattatttta    4740
tagaaactat tcttaaagac aaacgtggtt ataaacaaaa gccattaccc tagagcggcc    4800
gccaccgcgg tggagctcca gcttttgttc cctttagtga gggttaattt cgagcttggc    4860
gtaatcatgg tcatagctgt ttcct                                          4885
```